United States Patent
Grbic et al.

(10) Patent No.: US 9,848,856 B2
(45) Date of Patent: Dec. 26, 2017

(54) VALVE MODELING WITH DENSE CHORDAE FROM MEDICAL SCAN DATA

(71) Applicant: Siemens Medical Solutions USA, Inc., Malvern, PA (US)

(72) Inventors: Sasa Grbic, Princeton, NJ (US); Tommaso Mansi, Plainsboro, NJ (US); Ingmar Voigt, Erlangen (DE); Julian Krebs, Erlangen (DE)

(73) Assignee: SIEMENS MEDICAL SOLUTIONS USA, INC., Malvern, PA (US)

( * ) Notice: Subject to any disclaimer, the term of this patent is extended or adjusted under 35 U.S.C. 154(b) by 0 days.

(21) Appl. No.: 14/971,254

(22) Filed: Dec. 16, 2015

(65) Prior Publication Data

US 2016/0171766 A1 Jun. 16, 2016

Related U.S. Application Data

(60) Provisional application No. 62/092,586, filed on Dec. 16, 2014.

(51) Int. Cl.
| | | |
|---|---|---|
| A61B 34/10 | (2016.01) | |
| A61B 17/00 | (2006.01) | |
| G06T 7/00 | (2017.01) | |
| G06T 7/246 | (2017.01) | |
| A61B 6/03 | (2006.01) | |
| A61B 6/00 | (2006.01) | |

(Continued)

(52) U.S. Cl.
CPC ............ *A61B 17/00* (2013.01); *G06T 7/0016* (2013.01); *G06T 7/251* (2017.01); *A61B 6/032* (2013.01); *A61B 6/503* (2013.01); *A61B 6/52* (2013.01); *A61B 6/5217* (2013.01); *A61B 8/12* (2013.01); *A61B 8/488* (2013.01); *A61B 8/5223* (2013.01); *A61B 2017/00783* (2013.01); *A61B 2034/104* (2016.02); *A61B 2034/105* (2016.02); *A61B 2576/023* (2013.01); *G06T 2207/30048* (2013.01)

(58) Field of Classification Search
None
See application file for complete search history.

(56) References Cited

U.S. PATENT DOCUMENTS

| | | |
|---|---|---|
| 2010/0240996 A1 | 9/2010 | Ionasec et al. |
| 2012/0232386 A1* | 9/2012 | Mansi .................. A61B 8/0883 600/437 |

(Continued)

OTHER PUBLICATIONS

Kanik, Jingjing, et al. "Automatic personalization of the mitral valve biomechanical model based on 4d transesophageal echocardiography." International Workshop on Statistical Atlases and Computational Models of the Heart. Springer Berlin Heidelberg, 2013.*

(Continued)

*Primary Examiner* — Ryan D McCulley

(57) ABSTRACT

In valve modeling from medical scan data, chordae are modeled as a dense structure. Rather than attempting to provide the same number of chordae (e.g., 25) as found in a human valve, hundreds or thousands of chordae connectors are used. Since solving for lengths of so many chordae may be computationally intensive, the lengths of only a few are solved, and the lengths of the rest of the chordae are derived from the lengths of the few.

19 Claims, 6 Drawing Sheets

(51) Int. Cl.
  *A61B 8/12* (2006.01)
  *A61B 8/08* (2006.01)

(56) References Cited

U.S. PATENT DOCUMENTS

2014/0071125 A1* 3/2014 Burlina .................. G06T 7/246
                                                        345/420
2015/0059754 A1* 3/2015 Chbat .................... A61B 5/085
                                                        128/204.23

OTHER PUBLICATIONS

Marom, Gil, et al. "Aortic root numeric model: Annulus diameter prediction of effective height and coaptation in post-aortic valve repair." The Journal of thoracic and cardiovascular surgery 145.2 (2013): 406-411.*
Sprouse, Chad, Ryan Mukherjee, and Philippe Burlina. "Mitral valve closure prediction with 3-d personalized anatomical models and anisotropic hyperelastic tissue assumptions." IEEE Transactions on Biomedical Engineering 60.11 (2013): 3238-3247.*
U.S. Appl. No. 14/259,801, filed Apr. 23, 2014.
U.S. Appl. No. 14/735,203, filed Jun. 10, 2015.
Grbic, Sasa, et al. "Complete valvular heart apparatus model from 4D cardiac CT." Medical image analysis 16.5 (2012): 1003-1014.
Ionasec, Razvan Ioan, et al. "Patient-specific modeling and quantification of the aortic and mitral valves from 4-D cardiac CT and TEE." Medical Imaging, IEEE Transactions on 29.9 (2010): 1636-1651.
Mansi, Tommaso, et al. "An integrated framework for finite-element modeling of mitral valve biomechanics from medical images: application to MitralClip intervention planning." Medical image analysis 16.7 (2012): 1330-1346.

* cited by examiner

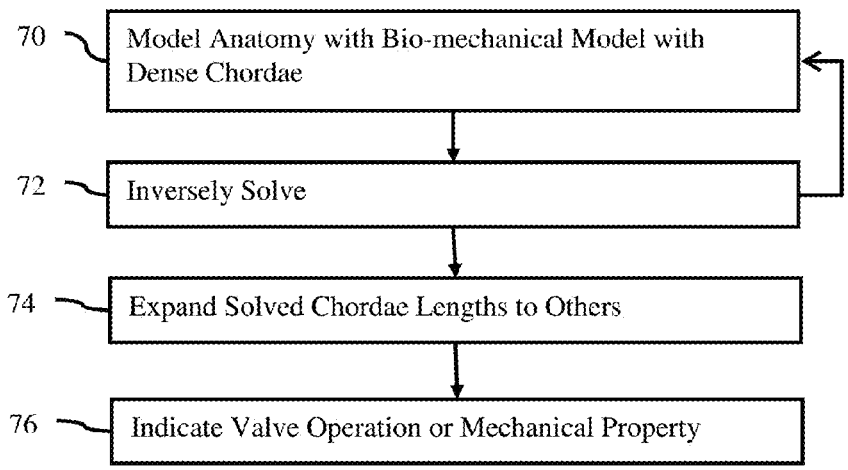
FIG. 7
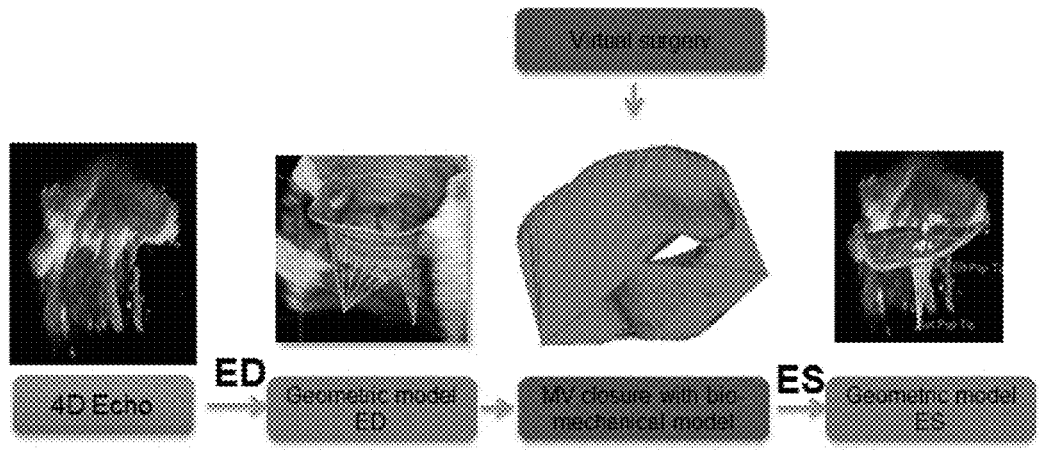
FIG. 8     systole – ES, diastole – ED

VALVE MODELING WITH DENSE CHORDAE FROM MEDICAL SCAN DATA

RELATED APPLICATIONS

The present patent document claims the benefit of the filing dates under 35 U.S.C. §119(e) of Provisional U.S. Patent Application Ser. No. 62/092,586, filed Dec. 16, 2014, which is hereby incorporated by reference.

BACKGROUND

The present embodiments relate to modeling of anatomy, such as the mitral valve. Medical imaging data is used to create patient-specific modeling.

Medical imaging techniques provide powerful tools to visualize valvular structures. Echocardiography (e.g., 4D Transesophageal Echocardiography (TEE)) is used in many clinical applications because of high temporal resolution, ease of use, and relatively low cost. Advancements in imaging techniques may allow for quantitative evaluation of the mitral valve structure to aid predictive surgical planning.

Several approaches have been proposed to model mitral valve geometry and dynamics, including morphological and biomechanical models. The morphological models employ an automatic or semi-automatic method to detect the mitral apparatus and track motion from medical images. These models provide visualization and quantitative measurements of the anatomical structure, but do not provide the underlying mechanisms of the motion pattern or pathological changes.

Several patient-specific biomechanical models, including structural models and fluid-structure interaction models, have been proposed using geometric information from medical images and general (e.g., population based) material parameters of the mitral leaflet tissues from experimental results. Mechanical models describing the mechanism of mitral valve dynamics may be useful to predict how the pathological dynamics can be modified by medical intervention. Such models have the potential to become efficient predictive tools to design preoperative treatment plans in selecting the patients and determining clipping sites to ensure the optimal outcome. However, the use of general material parameters limits the representation for specific patients, resulting in the model being of less use for diagnosis and surgical planning for a given patient.

The patient-specific biomechanical models may model structure not easily identified from medical imaging. For example, chordae are modeled as springs or connectors between leaflets and papillary tips. Attempting to model complex chordae structure with the simple connectors or springs may result in artifacts.

BRIEF SUMMARY

By way of introduction, the preferred embodiments described below include methods, computer readable media, and systems for valve modeling from medical scan data. Chordae are modeled as a dense structure. Rather than attempting to provide the same or similar number of chordae (e.g., 25) as found in a human valve, hundreds or thousands of chordae connectors are used. Since solving for lengths of so many chordae may be computationally intensive, the lengths of only a few are solved with optimization, and the lengths of the rest of the chordae are derived from the lengths of the few.

In a first aspect, a method is provided for valve modeling from medical scan data. A processor models a valve of a patient with a biomechanical model, which is a function of chordae lengths for a dense number of chordae relative to human anatomy, from the first medical image data representing the valve at a first time. The processor inversely solves for values of a sub-set of the chordae lengths of the valve as a function of differences between locations of the biomechanical model simulated for a second time and second anatomy locations detected from second medical image data representing the valve at the second time. The values of the chordae lengths for chordae lengths other than the sub-set are derived from the values of the chordae lengths for the subset. Valve operation is indicated from the biomechanical model with the values of the chordae lengths for the sub-set and the others.

In a second aspect, a non-transitory computer readable storage medium has stored therein data representing instructions executable by a programmed processor for valve modeling. The storage medium includes instructions for: modeling a valve of a patient with a finite-element model, the finite-element model including more chordae than in a human for each of at least four regions of the valve; inversely solving for lengths of one of the chordae in each of the at least four regions; and calculating lengths of others of the chordae in each of the at least four regions based on the regions of which the chordae are members and the corresponding lengths for the one of the chordae.

In a third aspect, a system is provided for valve modeling from medical scan data. An ultrasound scanner is configured to scan a heart volume of a patient, the scan providing medical diagnostic ultrasound data representing at least a part of the heart. A processor is configured to solve for a first chordae length in each of multiple zones and determine other chordae lengths in each of the multiple zones from the first chordae length for the respective zone. A display is configured to generate a visualization based on the first and the other chordae lengths.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 7 is a flow chart diagram of one embodiment of a method for valve modeling from medical scan data using dense chordae representation;

FIG. 8 illustrates one embodiment of inverse solution in modeling a valve;

DETAILED DESCRIPTION OF THE DRAWINGS AND PRESENTLY PREFERRED EMBODIMENTS

Figure 1:
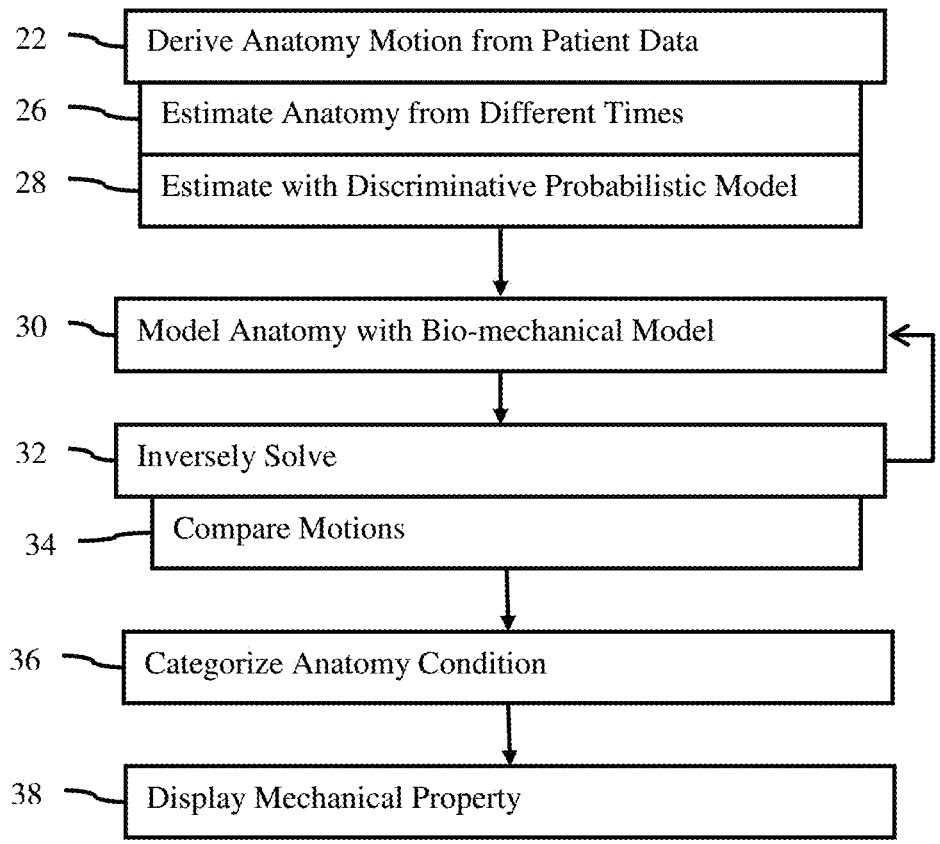
FIGS. 1-3 are flow chart diagrams of different embodiments of a method for estimating a mechanical property of anatomy.

Dense chordae are used in finite-element modeling of mitral valve biomechanics from medical images. Computational models of the mitral valve exhibit potential for patient-specific surgical planning. A finite-element model (FEM) of mitral valve physiology may be used to study the biomechanical impact of mitral valve repair. In one model, an integrated approach utilizes finite-element modeling of the mitral valve closure based on patient-specific anatomies and boundary conditions.

Inverse modeling is used to solve for the chordae length. The inverse modeling approach automatically personalizes the lengths of the chordae. In inverse modeling, the mitral valve closure geometry during systole is based on the geometrical model extracted from the mitral valve model derived from echo data captured during diastole. Section I below and FIGS. 1-6 are directed to some example finite-element models where chordae length and other model parameters are solved inversely.

A simplistic sparse chordae topology model is used in the model of Section I. Section II and FIGS. 7-11 extend the model by utilizing a dense chordae representation. The dense chordae representation in the biomechanical model may more accurately predict mitral valve function. The inverse solution is used, but by solving the lengths of fewer than all of the dense chordae. The lengths of the other chordae are derived from the lengths determined through inverse solution. By using inverse solution for fewer than all chordae, computational burden from the dense chordae representation is reduced.

Section I

One or more mechanical properties of anatomy, such as a mitral valve, are estimated from medical scan data of a patient. The mechanical properties are estimated for a specific patient rather than using generalized estimates. An inverse analysis framework combines image-based and biomechanical models to estimate the patient specific material property of anatomy and generate physically constrained motion. For example, the material parameters of the leaflets and the regional heterogeneity in distribution (anterior and posterior leaflets) for a given patient may be determined. The patient-specific regional material property enables the mechanical model to closely simulate, in vivo, mitral valve dynamic motion. In this way, the comprehensive patient-specific model may serve as a basis for predictive and efficient functional simulation to understand the anatomy function, design a surgical plan and assess a treatment outcome.

Any anatomy may be modeled, such as the heart, heart chamber, vessel, arteries, liver, lungs, or other part of a patient subjected to motion. In the example embodiments discussed herein, the mitral valve is used as an example. In other embodiments, more than one heart valve is identified and parameterized at a same time or during a same imaging session. For example, the mitral valve and the aortic valve are physiologically modeled. The whole heart, half the heart, or other sub-portion of the heart may be modeled.

The mitral valve is small and relatively rapidly moving. As a result, the types of imaging used to view the mitral valve may be limited, such as using ultrasound. With these limited types of imaging, it may be difficult to diagnose or plan from images alone given temporal and/or spatial resolution limitations due to the speed and small size of the mitral valve. Mechanical properties and modeling of the mitral valve may provide additional information.

In one embodiment, transesophageal echocardiography (TEE) is used to scan cardiovascular morphology for diagnosis, treatment planning and assessment and surgical guidance. The high quality four-dimensional (volume over time) TEE imaging allows for the analysis of not only the geometry but also the dynamics of the mitral valve. This morphological modeling may not provide patient-specific tissue properties.

Using the TEE imaging, an inverse analysis algorithm combines image-derived mitral valve dynamics and a biomechanical model to estimate patient-specific material parameters, interpolate the underlying mechanism of mitral valve kinematics, and refine the motion estimation. The refined motion estimation is constrained by the biomechanical model with personalized material parameters, so more likely matches each patient's mitral valve function better than if a generalized material parameters were used. Physiologically significant information may be determined. The patient-specific material property enables more reliable predictive surgical simulation and treatment decision.

Patient-specific computational models including morphological and biomechanical models based on medical images may provide quantitative information to aid clinicians for mitral valve (MV) disease management. Morphological models focus on extracting geometric information by automatically detecting the mitral valve structure and tracking structure motion from medical images, such as from TEE scan data. Biomechanical models are primarily used for analyzing the underlying mechanisms of the observed motion pattern. Patient-specific biomechanical models integrate the personalized mitral apparatus and boundary conditions estimated from medical images to predicatively study the pathological changes and conduct surgical simulations. For further patient specificity, one or more material properties of the biomechanical model are determined using the inverse solution. For one approach involving the mitral valve, the algorithm achieves the customization by adjusting both the chordae rest length and other material parameters, such as Young's modulus, which are challenging to estimate or measure directly from the medical images. The algorithm first estimates the mitral valve motion from scan data using a machine learning method and then incorporates the biomechanical model generated motion into the scan data-based estimation by minimizing the Euclidean distances between the two for the inverse solution.

Material properties vary among patients, especially in diseased areas. By enforcing consistency of imaging and model-derived motion, one or more material properties may be estimated using the modeling and scan data for a patient without intervention. An image-based automatic patient-specific model provides for automatic personalization of the valve biomechanical model by minimizing the Euclidean distances between model generated and image based mitral valve closure.

FIG. 1 shows a method for estimating a patient-specific material property of anatomy. The method is implemented by a medical diagnostic imaging system, a review station, a workstation, a computer, a PACS station, a server, combinations thereof, or other device for image processing medical data. For example, the system or computer readable media shown in FIG. 6 implements the method, but other systems may be used. A processor of any type of system, interacting with memory, user input, display, and/or other components, may perform the acts.

Figure 2:
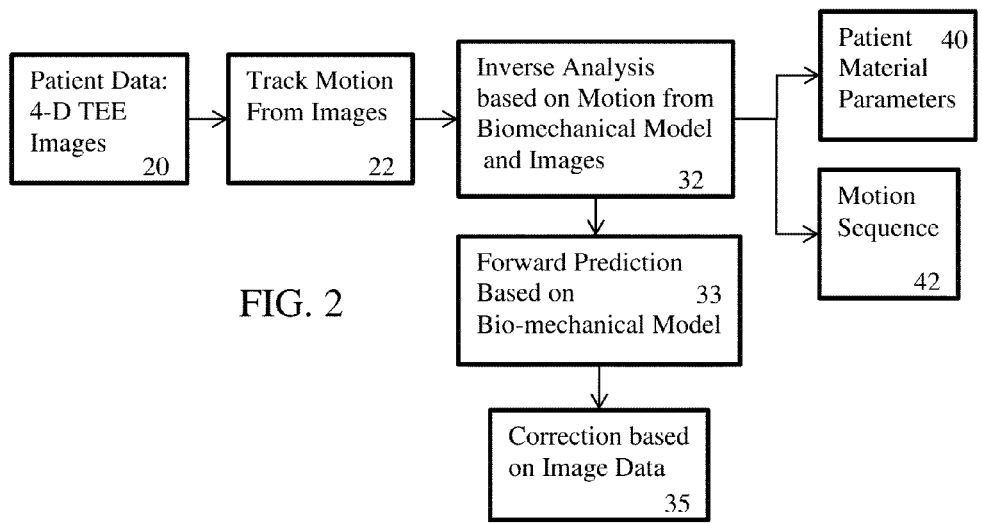

FIG. 2 shows another embodiment of the method for estimating a patient-specific material property. The method of FIG. 2 is similar to the method of FIG. 1, but highlights different aspects of the flow. For the method of FIG. 2, the patient-specific material parameters and physiologically significant motion from is estimated from 4-D TEE images 20. The proposed method is a two-step procedure: first, extract the mitral valve geometry sequence from the images in act 22, and then treat the motion sequence as an observation of the outcome of the mitral valve system in act 33 and perform inverse analysis in act 32 to fit in act 35 the image-based observation into the biomechanical model. An extended Kalman filter approach is used for the inverse analysis to produce a sequence of kinematics states 42 and material parameter estimates 40.

Figure 3:
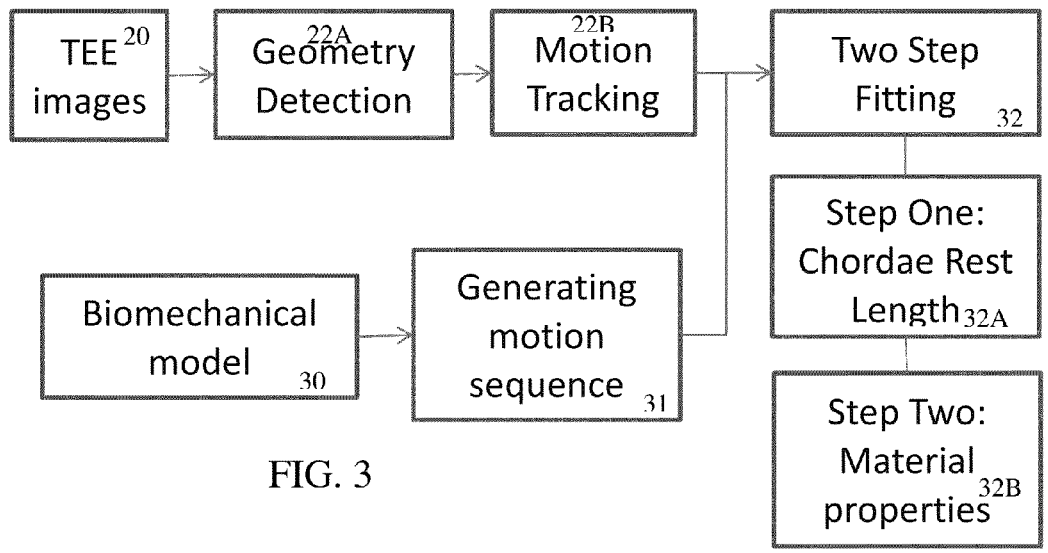

FIG. 3 shows yet another embodiment of the method for estimating the patient-specific material property. The method of FIG. 3 is similar to the methods of FIGS. 1 and 2, but highlights different aspects. The mitral valve closure process from the end diastole is studied, but the opening process may instead or additionally be studied. Diastole is the last frame ($I_0$) where the mitral valve is seen fully open in TEE images 20. The closure motion continues until the first systolic frame ($I_N$) where the mitral valve is seen maximally closed. The algorithm first estimates the leaflet geometry at the nth frame ($g_n$) in act 22A and tracks motion in act 22B to ensure inter- and intra-patient point correspondence of the geometric representation. Inter-point correspondence requires relationships among anatomy seen across patients. The intra-point correspondence requires relationships across time for a given patient. The biomechanical model 30 is used to generate a motion sequence ($h(g_0, m)$) in act 30. The biomechanically modeled motion is fit to the image-based observation by adjusting a set of patient-specific material parameters (m) of the biomechanical model in act 32. In one example, the material parameters are composed of leaflet biomechanical parameters (e.g., Young's modulus of different parts and the chordae rest length). The estimation problem is formulated as:

$$m = \min_m f(m) = \min_m |g_n - h(g_0, m)|$$

where the cost function is represented by the Euclidean distances between the biomechanical model generated and image observed mitral valve closure. The personalization is achieved by minimizing the cost function to obtain the patient-specific parameters. The cost function may be modified to penalize the mismatch in degree of coaptation for certain clinical applications when matching at the leaflet edge is more important than other regions. To solve the optimization problem, a two-step procedure is followed where chordae rest length is first solved in act 32A and then other material properties (e.g., Young's moduli of the leaflets) are solved in act 32B. The two procedures may be combined into one—solving for both at a same time. Other divisions or reverse order may be used.

The methods of FIGS. 1-3 are implemented in the order shown or a different order. Additional, different, or fewer acts may be performed. For example, the categorization and/or display of acts 36 and 38 of FIG. 1 are not performed. As another example, act 28 is not performed.

The acts may be performed in real-time, such as during scanning. The model may be parameterized or generated while scanning to acquire another dataset representing the volume. The acts may be performed during an appointment or off-line in a review period. The patient-specific data may be associated with previous acquisition rather than in real-time. Measurements and/or images of automatically detected anatomy may be provided in seconds, such as 10 or fewer seconds. Alternatively, the acts are performed as desired by a clinician regardless of whether a patient is currently at the facility or being scanned.

The acts may be performed automatically by a processor. The user causes the patient to be scanned or obtains scan data for the patient from a previous scan. The user may activate the process. Once activated, the anatomy is identified, and patient-specific values of one or more material properties are determined without further user input. User input of locations of the anatomy in any of the scan data may be avoided. Some user input may be provided, such as for changing modeling parameter values, correcting detected locations, and/or to confirm accuracy.

The models are based on scan data from a patient acquired in act 20 (see FIGS. 2 and 3). This patient-specific modeling may result in the anatomy locations and/material properties being different for different patients. For one patient, the material property (e.g., chordae length and/or Young's modulus) may be different than an average or another patient. Since the modeling relies on the patient-specific scan data, patient specific properties may be determined.

For patient specific modeling, one or more sets of scan data are obtained. Ultrasound, magnetic resonance, or computed tomography data is obtained. In one embodiment, 4D computed tomography data is used as disclosed in U.S. Pat. No. 8,009,887. Any medical imaging modality capable of scanning a volume multiple times during a heart cycle may be used, such as TEE echocardiography. The ultrasound scan data corresponds to a data set interpolated to a regular 3D grid, displayed images (e.g., detected and scan converted ultrasound data), beamformed data, detected data, and/or scan converted data. Imaging data may be a frame or volume of data representing a volume. The imaging data may be data from the processing path derived before generating an image or data for a display as an image. A frame or volume of data may be data in an image format or data in a different format (e.g., scan format or representing a three-dimensional grid). The ultrasound data represents a volume or 3D region of a patient.

The volume region includes tissue, fluid, or other anatomy structures. Different structures or types of structures react to the acoustic energy differently. The shape of a structure or spatial aspect may be reflected in B-mode or harmonic data. The flow of fluid may be reflected in color flow, Doppler, spectral Doppler, or Doppler flow data.

In act 22, motion of the anatomy is derived from the scan data of the patient. For example, motion of the mitral valve is estimated. Locations for different parts of the valve are calculated. The locations for anterior and posterior papillary tips, mitral annulus, and anterior and posterior leaflets are estimated (act 22A). A mesh representing the valve is estimated. The papillary heads may be located for chordae. Additional, different, or fewer anatomic locations may be used, such as the papillary tips. For patient-specific estimation, the locations of the anatomy are estimated using medical diagnostic data of the patient. The medical diagnostic data may be scan data, such as image data. Image data is used to include scan data or data to be processed into an image as well as data of a displayed image. Data representing the valve or volume of the heart is used for determining the locations of the anatomy. For estimating from the model relative to a particular patient, patient-specific aortic-mitral model estimation is provided from patient-specific scan data.

The processor estimates an anatomy model of the valve of a patient from the medical diagnostic imaging data of the patient. The estimation is data-driven. For determining the location, shape, motion, size or other characteristic of a heart valve, the valve is modeled generally. The model is fit to patient specific data by estimation. Any estimation may be used, such as disclosed in U.S. Published Patent Application No. 2010/0240996, the disclosure of which is incorporated by reference. The estimation is performed in sequential stages, such as associated with a hierarchal model. For example, a location of the global valve relative to the heart volume is estimated, one or more locations in the valve relative to other portions of the valve are then estimated, and then a surface of the valve is estimated. Each stage may use the same or different algorithms. For example, separate machine-learnt algorithms are used for each stage. Different models may be estimated from the frames of data for different stage, phase, or type of anatomy.

In one embodiment, a physiological model of the aortic and mitral valves is designed to capture complex morphological, dynamical, and pathological variations. The hierarchical definition is constructed on three abstraction levels: global location and rigid motion model, non-rigid landmark motion model, and comprehensive aortic-mitral model. Along with the parameterization, an anatomically driven re-sampling method to establish point correspondence required for the construction of a statistical shape model is provided. A collision detection and repair algorithm may provide physiological consistency.

To capture a broad spectrum of morphological variations, the model is parameterized by three coarse-to-fine components: i) three transformations B for global location, orientation and scale over the cardiac cycle; ii) the trajectories of ten anatomical landmarks $L(B)=(l1 \ldots l10) \in R^{3 \times 10}$ (e.g., two trigones, one posterior annulus mid-point, two commissures, two leaflet tips and three papillary tips); and iii) a triangulated surface mesh $S_{LA}(B, L)$ to represent the left atrial (LA) surface of both anterior and posterior leaflets. The positions of the vertices of the LA surface are constrained by the anatomical landmarks, resulting in an anatomically consistent parameterization that ensures intra- and inter-patient point correspondence.

Other meshes may be used, such as tetrahedral mesh. The estimated mesh represents the valve. The mesh represents a surface of the valve. Different surfaces, S, are determined for the different times or phases of the heart cycle. In one embodiment, the surfaces, S, are each a point distribution model of 986 points and 1792 triangles with consistent parameterization derived from anatomical landmarks (three trigones, three commissures, two leaflet tips and three papillary heads). Other numbers of vertices and/or triangles may be used.

Since it is still difficult to measure the thickness of the leaflets reliably, the thickness is set to a value, such as 2 mm (e.g., an average measure for all patients). In one example, the one layer leaflet surface mesh is extruded towards the ventricle for a set distance, which is 1.32 mm and 1.26 mm for the anterior and posterior leaflet, respectively, thus forming a volumetric structure. The single layer mesh of the leaflets is shifted towards the left ventricle in the direction of the surface normal to construct the volumetric structure. Next, the volumetric structure is discretized into tetrahedral meshes. The tetrahedral mesh is generated from this volumetric structure for the biomechanical model.

Any model may be used. In one embodiment, the estimation is a function of a discriminative probabilistic model in act 28. The model detects the locations of anatomy based on probability. The location associated with a highest probability, after any weighting or other consideration, is selected as the location for the anatomy. Different locations have different probabilities for representing the anatomy of interest. One type of discriminative probabilistic model is a machine-learned model. Other models may be used.

Combinations of different types of models may be used for the anatomy model. For example, different detectors are employed for the mitral annulus and free-edges contours and the leaflet surfaces to improve detection accuracy.

The anatomy model is estimated from the patient specific data. The patient specific data is an input feature to the model, such as a machine-learned matrix. In one embodiment, B, L(B) and $S_{LA}(L, B)$ are estimated from the frames of data using a hierarchical discriminative learning algorithm. The probability p(B, L, S|I), given the frame of data I, is incrementally modeled within the Marginal Space Learning (MSL) framework, based on the Probabilistic Boosting Tree (PBT). Given a test image, the MLS framework finds position candidates around the MV based on Haar and/or steerable features. The position candidates are then successively refined by rotation and scaling candidates. This defines a region of interest inside which the positions of ten landmarks are estimated using the same strategy.

In one embodiment, a robust learning-based algorithm, which in concordance with the hierarchical parameterization, includes three stages: global location and rigid motion estimation, non-rigid landmark motion estimation and comprehensive aortic-mitral estimation. Each stage may be implemented differently. In one embodiment, trajectory spectrum learning (TSL) with local-spatio-temporal (LST) features is used for the non-rigid landmark motion estimate. The number of stages may be fewer or more. The same algorithm is used for either ultrasound or computer tomography data. Alternatively, different algorithms are trained for the different types of data.

Any machine training may be used for one or more stages. The machine-trained classifier is any one or more classifiers. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used. Error-correcting output code (ECOC) may be used.

The classifier is trained from a training data set using a computer. Any number of expert annotated sets of data is used. For example, about 200 hundred volume sequences representing the heart and including one or more valves are annotated. The annotation indicates valve landmarks and/or surfaces within the volumes. The different anatomies of each volume are annotated. This large number of annotations allows use of a probabilistic boosting tree to learn relevant features over a large pool of 3-D Haar, and/or steerable features. Both features may be efficiently computed and be effective as a feature space for boosting classifiers. Other features may be used. Each classifier uses the data sets and annotations specific to the anatomy being classified.

In one embodiment, the classifier is a knowledge-based probabilistic model, such as marginal space learning using a hierarchical search. A database of known cases is collected for machine learning, providing a database-driven knowledge-based approach. For training data, three-dimensional context information is preserved and guides the detection process. Training and detecting the location of measurement indicators include detecting the associated anatomy since the measurement indicator indicates the anatomy. The classifier learns various feature vectors for distinguishing between a desired anatomy and information not being detected. In alternative embodiments, the classifier is manually programmed.

For learning-based approaches, the classifier is taught to distinguish based on features. For example, the probability model algorithm selectively combines features into a strong committee of weak learners based on Haar-like local rectangle filters whose rapid computation is enabled by the use of an integral image. Features that are relevant to the anatomies are extracted and learned in a machine algorithm based on the experts' annotations, resulting in a probabilistic model. A large pool of features may be extracted. The training determines the most determinative features for a given classification and discards non-determinative features. Different combinations of features may be used for detecting different anatomies, the same anatomy at different resolutions, and/or the same anatomy associated with different translation, rotation, or scale. For example, different sequential classification stages utilize different features computed from the 3D volume data. Each classifier selects a set of discriminative features that are used to distinguish the positive target from negatives. The features are selected from a large pool of features. The large pool is determined by a programmer or may include features systematically determined.

A tree structure may be learned and may offer efficiency in both training and application. In the midst of boosting a multi-class classifier, one class (or several classes) may have been completely separated from the remaining ones and further boosting yields no additional improvement in terms of the classification accuracy. For efficient training, a tree structure is trained. To take advantage of this fact, a tree structure is trained by focusing on the remaining classes to improve learning efficiency. Posterior probabilities or known distributions may be computed, such as by correlating anterior probabilities together.

To handle the background classes with many examples, a cascade training procedure may be used. A cascade of boosted binary-class strong classifiers may result. The cascade of classifiers provides a unified algorithm able to detect and classify multiple objects while rejecting the background classes. The cascade structure corresponds to a degenerate decision tree. Such a scenario presents an unbalanced nature of data samples. The background class has voluminous samples because all data points not belonging to the object classes belong to the background class. Alternatively, the classifiers are sequentially trained without cascade.

The probabilistic boosting tree (PBT) unifies classification, recognition, and clustering into one treatment. A probabilistic boosting tree is learned for each anatomy or stage of interest. The classifier is a tree-based structure with which the posterior probabilities of the presence of the anatomy of interest are calculated from given data. Each detector not only provides a binary decision for a given sample, but also a confidence value associated with the decision. The nodes in the tree are constructed by a combination of simple classifiers using boosting techniques.

By inputting the patient-specific data, the anatomy model is estimated for a given patient. The locations for the anatomy are estimated for a given time, such as end-diastole, and/or for a sequence of times, such as throughout a heart cycle. The anatomy model may include input information not obtained from the scan data.

Figure 4:
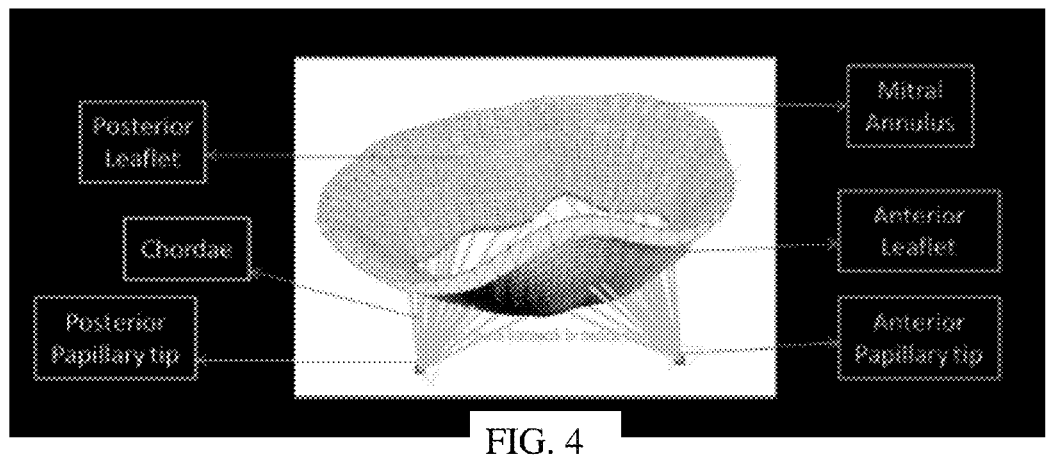
FIG. 4 is an illustration of example landmarks and mesh for a heart valve.

The anatomy model may include a mesh fit to the valve based on the detected anatomy (see FIG. 4). The model outputs the mesh or the mesh is formed based on the locations of anatomy output by the model. The point-distribution model of the MV surface is mapped according to the landmarks and deformed, within the learned space of shapes, according to boundary detectors estimated through PBT.

The same or different model or group of models is used for the initial identification of anatomy locations. For example, the locations are detected in a first iteration or in preparation for a first iteration. For later iterations, the locations (e.g., surface, area, line, or point) are refined. The model may accept as input the frame of scan data and/or the surface. In one embodiment, the surface position is refined by using a previously detected surface and the patient-specific data as inputs to the model. The refining uses a machine-learned matrix of a discriminative probabilistic model. The initial detection uses the same or different machine-learned matrix.

The mitral annulus and papillary tips motion are also quantified from the images to be used as prescribed information in the biomechanical model. The marginal and basal chordae are attached between papillary head and leaflet free edges. The insertion points are determined by visual inspection, such as based on user input relative to an image. The complete mitral valve geometry is shown in FIG. 4, and the blue trajectories indicate the mitral annulus and papillary tips motion. The morphological model represents a volumetric structure, including fiber orientation and modeling of the chordae.

The locations for the same anatomy at different times are found in act 26. The same or different model is used for detecting the anatomy at different phases. The method may be performed for two frames representing different times. The heart cycle is cyclical, so has phases. Example phases are diastole and systole. The method is performed on two frames of data from different times and representing different phases of the heart cycle. For example, one frame represents diastole and the other frame represents the heart volume 0.05-0.3 seconds later.

The method may be applied on the entire 4D time series of frames, such as performing the method for a moving window of pairs of frames throughout the cycle. Any number of frames for a given cycle and corresponding phases may be used, such as 2-40. The frames representing different phases may be acquired from different cycles, but are temporally positioned to represent the heart over a cycle. The description below is for two frames $I_{t1}$ and $I_{t2}$ at times t1 and t2 only, for the sake of clarity.

The estimation is performed for each of the frames of data or different times as represented by act 22A. Since each frame is for a different phase, the estimates are of the locations of the anatomy at different times. The model parameters are estimated from volumetric sequences (3D+time data) to construct patient-specific aortic-mitral representations. For different times, independent estimation is used, or the determined locations are tracked in act 22B, such as using correlation or other tracking. The estimation for the different frames may initially be independent of estimation for other frames. For later iterations, the estimation for any given frame may be based, at least in part, on the estimated locations of the anatomy in frames representing other phases. The MV anatomy is tracked in act 22B over the cardiac sequence using a manifold-based motion model.

In act 30, the anatomy, such as the mitral valve, is modeled with a biomechanical model. The biomechanical model incorporates material properties rather than just the dynamic behavior of the morphological model.

To personalize the biomechanical model, the geometry or location information at a given phase or different phases may be incorporated into the biomechanical model. For example, the geometry at the end diastole is then further processed to be loaded into the biomechanical model. The mitral annulus motion and the papillary tip motion (e.g., trajectories or displacement) derived from the TEE images may be used as a boundary condition for the biomechanical model.

Fiber models are mapped on the leaflets where the fiber directions are mainly parallel to the annulus while those in the anterior leaflet close to the commissures gradually rotate to become perpendicular to the annulus. The chordae are attached between the leaflet and the papillary tips, such as determining the attachments for twenty-eight marginal chordae and eight basal chordae. The insertion points are determined by visual inspection and are identical for all the patients. Automatic placement of the insertion points may be provided. The geometry at early systole may be processed in a similar manner and used in the automatic personalization process.

The anatomy locations from different times are used as a starting point for the biomechanical model. The biomechanical model relates the physical mechanics of the valve from one time to another time. Based on the physics or physical structure, the biomechanical model is applied to determine the change in the anatomical locations over time to the given time.

For a pair of frames (e.g., closure and open), a converse alteration is performed. For time one, the locations from time two are used as the starting point for the biomechanical transform to time one. For time two, the locations from time one are used as the starting point for the biomechanical transform to time two.

The deformations between times are calculated by solution of a dynamic system. The dynamic system represents the change due to physical operation of the valve. For example, the dynamic system includes terms for mass, damping, stiffness, displacement, velocity, and acceleration. Additional, different, or fewer terms may be used to represent the operation of the valve.

In one embodiment, the dynamic system of the biomechanical model is represented as:

$$M\ddot{U}+C\dot{U}+KU=F_{ext}$$

where U is the displacement vector of the vertices of the mesh, $\dot{U}$ is the velocity of the vertices, and $\ddot{U}$ is the acceleration of the vertices, M is a diagonal mass matrix (e.g., leaflet mass density $\rho=1.04$ g/mL), C is a Rayleigh damping matrix (e.g., C=0.1(M+K)), and K is the stiffness matrix of the internal elastic forces. The tissue properties of the leaflets are represented as a linear isotropic material to optimize computational efficiency for fast estimation. The leaflet thickness is set to 2 mm or other value since imaging may not accurately represent this thickness. If the thickness information is available from imaging data, then the measured thickness may be used. The thickness is an average from representative patients, but other thicknesses may be used. Alternatively, leaflet thickness is solved for as a patient-specific material property. Near-incompressibility is achieved with a Poisson ratio v of 0.488 and a Young modulus E of 6.2 MPa. Alternatively, the Young's modulus and/or the Poisson ratio are solved as patient-specific material properties. Other dynamic representations of the biomechanical model may be used.

The leaflets are modeled as linear, transverse isotropic elastic tissues. The leaflets may behave as linear materials in the range of physiological pressures even if modeled throughout the cycle. Linear elasticity models are also computationally efficient, allowing fast simulations and real-time intervention planning. Any linear relationship may be used for basal and marginal regions, such as an initial generally inelastic region followed by a linear increase in elasticity as a function of force. In alternative embodiments, the curved lines or other representation of the leaflet tissue is used. The proposed method may also be applied if a non-linear model for leaflet mechanics in used in place of the linear model.

Different or the same tissue properties are assigned to the AL and PL, such as AL Young's modulus of $E_{ALf}=6.233$ MPa, $E_{Alf\perp}=2.350$ MPa, AL shear modulus of $G_{ff\perp}=1.369$ MPa, PL Young's modulus of $E_{PLf}=2.087$ MPa, $E_{PLf\perp}=1.887$ MPa, and PL shear modulus of $G_{ff\perp}=0.694$ MPa. Other values representing the tissue may be used. Alternatively, one or more region specific tissue properties are solved as patient-specific material properties.

In the dynamic system, the force, $F_{ext}$, applied for solving the biomechanical model emulates a spring. Other forces may be added or used instead of a spring force. The force is directional, such as at a normal to the anatomical location. The normal is at the surface for each location, such as at each vertex. Force at other directions may be used.

The force may be weighted. For example, the force is weighted by an amount of altering. Greater alterations may result in greater force. A difference in velocity, position, or acceleration of vertices from different times is used as the weight. The inverse relationship may be used. Other or no weighting may be used.

The force is calculated from the surface or other anatomy locations at one time for alteration of the anatomy locations for a different time. The surface for the one time is deformed based on the biomechanical model of the valve with the external force calculated from the surface used as the starting point. $F_{ext}$ is the external force that drives a location at one time towards the new estimate of the location. To make the result as close as possible while preserving the tangential motion generated by the internal forces, the vertices are moved long their normal direction n, towards their corresponding vertices at another time. In one embodiment, the force is weighted according to the uncertainty in the data term $\rho(v_{t1}|I_{t1})$ such that positions with low confidences have little influence on the leaflet deformation, while high confidences result in high influence. For example, $F_{ext}$ is written as:

$$F_{ext}(v_{t2}")=-\kappa\rho(v_{t1}'|I_{t1})(v_{t1}'-v_{t2}")\cdot n$$

where $\kappa$ is a weight parameter. Any value may be used, such as empirically setting $\kappa$ to 0.1.

In another embodiment, $F_{ext}$ is the total force developed by the chordae, $F_c$, and heart pressure, $F_p$. A generic profile that increases from 0 mmHg to 120 mmHg is used for the heart pressure. The force exerted by chordae is related to the material property, morphology, and elongation of the chordae, and may be solved for as patient-specific material properties or may be based on a generic representation. The force, $F_c$, induced by the chordae is calculated using the following equation: $Fc(v_i, p_i, t)=-k_{c,i}(\epsilon_{c,i}, t)\times(L_i(t)-L_{i,0})$ where $L_i(t)$ is the current elongation, $L_{i,0}$ is the chordae rest length, $\epsilon_{c,i}(t)=(L_i(t)-L_{i,0})/L_{i,0}$ is the strain, $k_{c,i}$ is the spring tensile stiffness and related to chordae material properties. Other force equations may be used.

For calculating motion, the biomechanical model is solved as a finite element model. The various components are spatially and temporally handled in discrete steps. The dynamics are solved as a linear system using acceleration, velocity and position.

In one embodiment, the vertices $v_{t2}"$, and thus the force, $F_{ext}$, are updated at every time step of the resolution of the dynamic system. The equation is solved using co-rotational triangular finite element methods (FEM) to cope with large deformations and rotations of the anatomy of the valve. An implicit Euler solver is employed to update mesh positions. The deformation ends when the average relative displacement of the surface vertices is lower than the image resolution (typically 1 mm). This solution is performed for each iteration.

The finite element modeling is performed without user input of anatomy locations. The user may activate the creation of models and simulation, but input of locations of anatomy is avoided. The simulation is performed automatically. In alternative embodiments, the user confirms or indicates locations of anatomy for creation of models or control of the closure simulation. For example, the user inputs chordae locations or insertion points.

The biomechanical model is a function of the motion and one or more patient-specific material parameters. For example, the Young's modulus, chordae rest length and/or other material parameters or other mechanical property are accounted for in the biomechanical model. One or more of these material properties may be solved for a patient-specific value. Other material properties may be assigned or predetermined, whether by measurement or by using a generalized or generic (e.g., average) value.

Since chordae may be difficult to visualize, chordae may be solved for patient-specific values. Chordae rest length may have a significant influence on the motion predicted by the biomechanical model. In one embodiment, 28 marginal chordae and 8 basal chordae are included in the biomechanical model as patient-specific material properties. The chordae may be divided in four groups based on the leaflet and papillary tip to which the chordae are attached.

Alternatively or additionally, Young's modulus is included as a patient-specific material property. The mitral leaflets are modeled as linear, transversely isotropic and nearly incompressible elastic tissues. The tissue material properties, including Young's modulus along and across the collagen fiber and shear modulus ($E_{ALf}$, $E_{ALf}\perp$, $G_{AL}$, $E_{PLf}$, $E_{PLf}\perp$, and $G_{PL}$, respectively) of the anterior and posterior leaflet are assumed to be different for different patients.

In one embodiment, the target set of patient-specific parameters are defined as m=[$E_{ALf}$, $E_{ALf}\perp$, $G_{AL}$, $E_{PLf}$, $E_{PLf}\perp$, $G_{PL}$, $L_{1MA}$-$L_{14MA}$, $L_{1MP}$-$L_{14MP}$, $L_{1BA}$-$L_{4BA}$, and $L_{1BP}$-$L_{14BP}$] where $L_{MA}$, $L_{MP}$, $L_{BA}$, and $L_{BP}$ are the chordae rest length of the marginal and basal chordae attached to anterior and posterior papillary tips. Only one, different, or additional patient-specific parameters may be used. Other material characteristics may be included. For example, more than one stiffness measure may be used for each chordae. The stiffness along a chordae may be different than the stiffness in a perpendicular direction. The other material parameters of the biomechanical model use non-patient-specific values.

Given values for the various material properties, the displacement from the morphological model (e.g., displacement measured from scan data), and any boundary conditions from the scan data, the biomechanical model may be used to estimate motion of the anatomy. Force is applied and the resulting motion of the modeled anatomy is determined. For a first iteration, default values may be used for the patient-specific material properties. The default values may be population based. Using the biomechanical model, the motion from one time to another (e.g., from end diastole to end systole) is determined for various locations, such as the mesh and other parts of the anatomy. The displacement or the end locations represent the motion.

In act 32, the patient-specific mechanical or material properties are solved for inversely. As part of the inverse solution, a forward projection of the motion using the biomechanical model is calculated in act 33. The forward projection uses values of the patient-specific properties, such as default or later refined values. The resulting biomechanically predicted motion is compared in act 35 to the morphologically modeled (e.g., motion from the scan data) motion. Motion may be compared in terms of a magnitude and direction of change, difference in positions, or position resulting from the motion. The comparison provides an indication of accuracy of the current patient-specific material properties. If converged or sufficiently resolved, the difference in motion for all or a sub-set of anatomy locations is below a threshold.

If above the threshold for any one or other number of locations, the solution is not converged. Other values of one or more patient-specific material properties are used. The changes may be altered sequentially, such as solving for one patient-specific material property and then another, or may be performed in parallel, such as solving for multiple values in each iteration.

The amount and/or direction of the change in values may be determined in an iterative solution. Any optimization or minimization may be used. In one embodiment, the non-linear function of the biomechanical function is solved with an extended Kalman filter. In other embodiments, other filtering with or without noise terms is used. In yet other embodiments, gradient descent or other optimization or minimization algorithms may be used. Non-gradient approaches may also be used. Any cost function may be used in the optimization problem.

By iteratively repeating the calculation of the motion with the biomechanical model using updated values for the patient-specific material properties and the comparison of the output motion with the detected motion from the patient, the values that result in the biomechanical model performing as indicated by the morphological model (i.e., detected motion) are found.

For the inverse solution, the dynamic equilibrium equation (i.e., biomechanical model) is transformed into state space representation of the system, provided by:

$$x_k = f(x_{k-1}) + w_{k-1} = x_{k-1} + w_{k-1}$$

$$y_k = k(x_k) + v_k$$

where $x_k$ is the material parameter vector at the kth image frame, which stays constant during the cardiac cycle, $y_k$ is the position of the mitral leaflet at the kth image frame, which is calculated by adding the reference position and displacement U, and $w_{k-1}$ and $v_k$ are the process and observation noises, respectively. Other representations may be used, such as without the noise variables. The displacement vector $U=K^{-1}(F-M\ddot{U}+C\dot{U})$ is a non-linear function of the material parameters, so the location $h(x_k)$ is also a non-linear function of $x_k$. To solve the system, an extended Kalman filter (EKF) adopts a prediction-correction process in the estimation. The material property of the mitral valve is identified by the recursive filtering procedure as following:

Initialization:

$$x_o = \mu, P_o = P_0 \quad (4)$$

Prediction:

$$x_k^f \approx f(x_{k-1}^a) \quad (5)$$

$$P_k^f \approx J_f(x_{k-1}^a) P_{k-1} J_f^T(x_{k-1}^a) + Q_{k-1} = P_{k-1} + Q_{k-1} \quad (6)$$

Kalman Gain:

$$K_k = P_k^f J_h^T(x_k^f)(J_h(x_k^f) P_k^f J_h^T(x_k^f) + R_k)^{-1} \quad (7)$$

Correction:

$$x_k^a = r_k^f + K_k(y_k - h(x_k^f)) P_k^f \quad (8)$$

$$P_k = (1 - K_k J_h(x_k^f)) P_k^f \quad (9)$$

where $J_f$ is the Jacobian matrix of f and an identical matrix I in this case, and $J_h$ is the Jacobian matrix. $h_i(x_k)$ is the position of ith element, and $\Delta x_{j,k}$ is the finite increment of the jth component of vector $x_k$. The formulation keeps the finite element method as an independent module and uses the output of the finite element method for the calculation of the Jocaobian matrix for Kalman filtering.

In one example embodiment, the inverse solution is used to solve for a plurality of mechanical properties, m, of the valve of the patient. The goal of personalization is to determine a set of parameters that minimizes the distance (f(m)) between the biomechanical model driven and the image-observed mitral valve closure. In this example, the chordae rest length and Young's modulus are solved sequentially in acts 32A and 32B. The first step aims to personalize the rest length using a coarse-to-fine maximum derivative method. This method may be represented as an example algorithm:

Algorithm 1 Coarse-to-Fine Maximum Derivative
1. Initialize the chordae rest length using the point-to-point distance from the papillary tip and the insertion points at the end systole;
2. At Jth level, change the group of the parameters in the direction of maximum derivative to reduce the cost function;
3. Repeat 2 until the cost function does not change between two consecutive iterations
4. Go to the (J+1)th level and repeat 2,3

Twenty-eight marginal chordae are used, fourteen attached to each leaflet and seven attached to each papillary tip. Eight basal chordae are used, four attached to each leaflet and two attached to each papillary tip. Fixing the material parameters, thirty-six parameters are to be estimated in the first step (m1=[$L_{1MA}$-$L_{14MA}$, $L_{1MP}$-$L_{14MP}$, $L_{1BA}$-$L_{4BA}$, $L_{1BP}$-$L_{4BP}$]). There are four levels from coarse-to-fine for the biomechanical models, but other numbers of levels and/or chordae may be used. Eight groups of the parameters are used in the first level following the chordae location where seven marginal chordae form one group, while two basal chordae form one group. The grouping becomes finer in each level. Seven groups of marginal chordae and eight groups of basal chordae are used in the second level. Fourteen groups of marginal chordae are used in the third level, and each of the marginal chordae rest length is estimated individually in the fourth level. Using coarse-to-fine solution provides better computational efficiency since the optimization at the coarse level provides a better starting point for finer tuning.

The second step of the algorithm aims to personalize material parameters using the extend Kalman filter (EKF) approach since EKF provides a stable sequential least square solution and may be efficient for material parameter estimation. Once the chordae rest length is fixed or solved, there are six parameters (m2=[$E_{ALf}$, $E_{ALf\perp}$, $G_{AL}$, $E_{PLf}$, $E_{PLf\perp}$]) to be estimated, four of which may be derived from the other two. The ratio of Young's modulus along and across the fiber ($r=E_f/E_f\perp$) is fixed or solved and the shear modulus is approximated by $G \approx Ef/(2((1+v)))$ to ensure the physiological consistency of the parameters. The state space representation is written as follows:

$$m_{2,k} = f(m_{2,k-1}) + w_{k-1} = m_{2,k-1} + w_{k-1}$$

$$g_k = h(m_{2,k}) + v_k$$

where $w_{k-1}$ and $v_k$ are the state and process noises, respectively, and assumed to follow Gaussian distributions with covariance matrix $Q_k$ and $R_k$, but other distributions may be used. The observation vector $gk=[x_{k1}, y_{k1}, z_{k1}, \ldots x_{ki}, y_{ki}, z_{ki}, \ldots x_{kL}, y_{kL}, z_{kL}]$ is the geometry vector, which is represented by L number of vertices (e.g., L=3248 but another number may be used). The process function f(·) is derived from the assumption that material parameters and the chordae rest length stay constant during the cardiac cycle. The observation function h(·) is derived from the biomechanical model specifying loading, geometry, tissue property, boundary condition, and dynamic equilibrium function and is the same as in the cost function (e.g., represented by Euclidean distances).

The EKF estimation is first initialized with the general material parameters ($m\hat{}_{2,0}$) and its covariance matrix (e.g., $Q_0$ equals the identity matrix) and then follows a prediction-correction iteration. In the prediction step, the targeted parameters $m^f_{2,k}$ are predicted to be the same as the last estimates. In the correction step, the predicted closure h($m^f_{2,k}$) using the predicted parameters $m^f_{2,k}$ is compared to the observation $g_k$ to generate new estimates $m^a_{2,k}$. The iterative process is stopped when the average distances of the locations of the patient-specific model and the locations of the image based estimation between two consecutive iterations are less than 0.01 mm or the maximum number of iteration is reached. The whole set of patient-specific parameters is obtained after the second step.

Using the inverse solution and the comparison of motion, the material properties, such as Young's modulus and/or rest length of at least two chordae, may be estimated for a patient in vivo. Scan data of the patient, without invasive measurements, is used to determine the material properties. Similarly, external force is not applied to the anatomy to determine the properties. A shear or longitudinal wave for elasticity imaging is not needed, so an acoustic force pushing pulse is not transmitted. Comparison of motion, such as displacements or positions resulting from displacement, between the observed and the biomechanical model, is used to find the properties.

In one embodiment, other information in addition to the biomechanical model is used. The solution of the patient-specific material properties also incorporates blood flow or other information. For example, the solution is a function of a Computational Fluid Dynamics (CFD) or a Fluid-Structure Interaction (FSI) model incorporating the biomechanical model. Invasive or non-invasively determined pressure, and/or flow measurements (Ultrasound Doppler, or Phase contrast MRI), or other source of fluid dynamics is included in the fluid-structure model, such as disclosed in U.S. Pat. No. 8,224,640. One or more aspects of the fluid dynamics may be solved in a patient-specific manner, such as solving for a pressure with the fluid-structure interaction model. Other or all fluid aspects may instead be used as observed information for matching in the solution or used as information for determining the material properties.

The material properties may be used in various ways. For example, the material properties are used in the biomechanical model to predict response to surgical intervention (e.g., performing a virtual surgery on the personalized model of the patient's anatomy) or for diagnosis from operation indicated by the biomechanical model. In act 36, one or more the patient-specific material properties are used to categorize a condition of the valve of the patient. The value of the material property is compared to a pre-determined value, such as an expected value. Tissue properties may be compared with a database of normal/abnormal tissue properties for patient stratification and/or diagnosis. For example, an abnormally high or low value may indicate a disease state for the valve. The tissue properties may be used for surgical and/or intervention planning. For example, the value of the material property may indicate whether surgical intervention is appropriate, in what way to intervene (e.g., minimally invasive, open surgery, or transcatheter), and/or an optimal approach for a given intervention.

Figure 5:
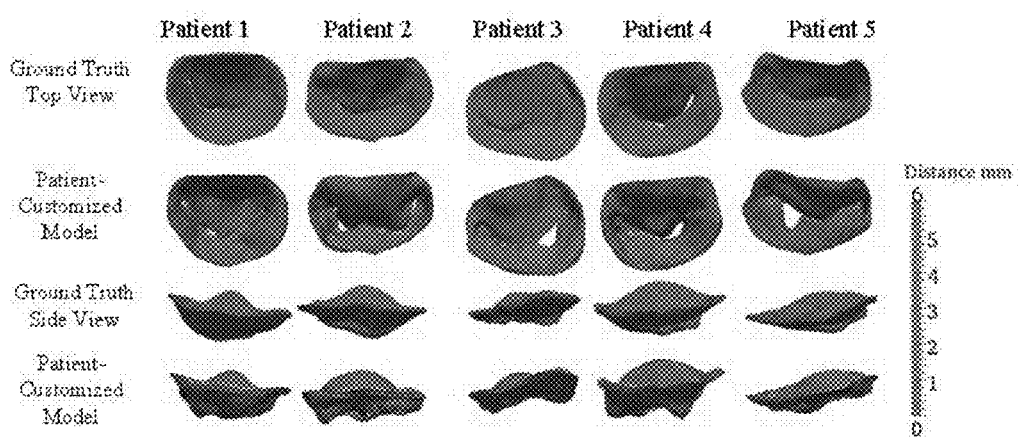
FIG. 5 illustrates example results of modeling heart valves.

In act 38, an image is displayed. The image is a function of the patient-specific value or values of one or more material properties. The value of the material property may be displayed, such as text or numbers in a list. In one embodiment, a position or sequence of positions (e.g., motion) of a model of the valve is displayed. The biomechanical model and corresponding mesh is used to generate an image. FIG. 5 shows examples of valve images for different patients from two different views. The biomechanical model uses the patient specific mechanical properties.

For imaging, an image of the valve is generated. The image is from the acquired scan data and/or from the biomechanical model. For example, the mesh representing the valve may be used for imaging. The image is a rendering of a three-dimensional volume. Voxels or data representing three-dimensional locations are rendered to a two-dimensional view. Ray casting, projection, surface or other rendering may be used. Two-dimensional planes may be alternatively be used.

In one embodiment, the surface is overlaid on a rendering of the heart or valves. The valve images are rendered from medical data with a same scale and perspective as an outline overlaid on the rendering. Color coding or other display modulation may be used with or in addition to an overlay. For example, different surfaces of the valve are rendered from B-mode data in gray scale with color modulation specific to the simulated surface. One surface may be rendered in one color and another in another color where brightness or shade is based on the material property.

One rendering or multiple renderings from the same volume may be displayed. In one embodiment, a sequence of images is displayed. The sequence is rendered from the different volumes throughout a portion (e.g., simulating closure) of or the entire heart cycle. For each image in the sequence, the corresponding detected or estimated valve information is displayed. The surface corresponding to the valve at the given time represented by an image is displayed. The images of the sequence may be displayed in succession to show or represent the motion of the valve. The representation of the valve is generated as a function of the surfaces simulated through the sequence.

In another embodiment, the tissue properties themselves are visualized. Some aspect of the image, such as color, shade, and/or brightness, is modulated as a function of the patient-specific values of the material properties. For example, the scan data is used to generate a three-dimensional rendering of the valve over time. The pixels for different regions of the valve are displayed with a color set based on the patient specific values. Any type of image of the valve may be generated, such as a polar plot or regional distribution image.

The displacement or motion used may be from opening to closure or closure to opening. Data for only two times is needed. In other embodiments, greater temporal resolution is used, such as using motion for three or more different times from closure to opening or opening to closure. The additional comparisons may lead to more accurate estimates of the material properties. Motion over a greater or lesser extent of time may be used, such as motion over an entire heart cycle. Different temporal windows or ranges of motion may be used to separately estimate the material properties. These separate estimates may be averaged or used separately for the biomechanical model for different phases of the cardiac cycle.

From the 4D anatomical or biomechanical model of the MV as constrained by the dynamic system, different metrics may be calculated. The dynamic change of the anterior-posterior (AP) annular diameter, computed as the difference diameter between early systole and early diastole, may discriminate the normal patients from functional mitral regurgitation patients. The change in diameter may indicate a reduced accentuation of the saddle shape with consequent reduction in leaflet coaptation. In addition to a dilated, akinetic annulus, the anterior surface length may be larger for patients with functional mitral regurgitation. The choice of ring size and type may be based on these automated measurements. Automated 3D quantitative surgical anatomy in FMR shows that an akinetic annulus is an early basis for MR, followed by annular dilatation and anterior leaflet lengthening, and that these mechanistic insights and the quantitative characterization of the pathological anatomy may aid surgical decision-making.

In one test, the method above is evaluated on datasets of simulated dynamic motion. The mitral valve geometry at an open state is used to generate the motion sequence. The material parameters are known when generating the motion sequence so the estimated material parameters may be compared to the ground truth. The material property is assumed to be homogeneous within the anterior and posterior leaflets but regionally different. Only two frames including the open and closed mitral valves are used to perform the parameter estimation since the closing state is the most important morphology when evaluating the mitral valve disease, such as mitral stenosis and regurgitation. Both the material parameters (Young's modulus in anterior and posterior leaflet, EA and EP) estimates and the refined closing state geometry to the simulated data, which is noise free, are compared to the ground truth. The results are shown in Table 1 where the point-to-mesh distance is the Hausdorf distance between two meshes.

TABLE 1

|  | s1 | s2 | s3 |
| --- | --- | --- | --- |
| EA True (MPa) | 6.2330 | 5.7880 | 6.2330 |
| EP True (MPa) | 6.2330 | 5.7880 | 4.3631 |
| EA Estimate (MPa) | 6.2714 | 5.8653 | 6.2101 |
| EP Estimate (MPa) | 6.2714 | 5.8653 | 4.6570 |

TABLE 1-continued

| Estimation error (%) | 0.62 | 1.27 | 3.55 ± 4.51 |
|---|---|---|---|
| Point-to-mesh distance (mm) | 0.0678 ± 0.0613 | 0.2030 ± 0.1864 | 0.0712 ± 0.0588 |

| | P1 |
|---|---|
| EA (MPa) | 7.8047 |
| EP (MPa) | 3.2530 |

The results demonstrate that the method accurately estimates the material parameters with less than 5% error and the refined motion with less than 1 mm point-to-mesh distance.

The proposed method is also tested on sets of patients' TEE images. Similarly, the geometry at open and closed state is used as the observation to perform the inverse analysis. It is difficult to validate the real material property for each patient since there is no direct measurement. So, the similar trend in the anterior and posterior parameters for normal patients is used to indicate validity.

| | General (mm) | Personalized (mm) |
|---|---|---|
| P1 | 2.4018 ± 1.0089 | 2.2280 ± 0.9200 |

In another verification, the automatic personalization algorithm is evaluated on the TEE images of five patients. First, the mitral valve apparatus and its motion are estimated from the TEE images using the machine learning method. The mitral leaflets are represented by tetrahedron finite elements with 9408 elements and 3248 vertices. Second, the mitral valve apparatus at the end diastole is loaded into the biomechanical model and the motion of the mitral annulus and the papillary tips are used as the prescribed boundary conditions. Third, the two-step personalization algorithm (e.g., acts 32A and 32B of FIG. 3) is applied by adjusting the chordae rest length and material parameters from a coarse-to-fine level. The initial value of the chordae rest length is determined by the point-to-point distance from the papillary tip and the insertion points at the end systole. The initial value of the Young's modulus at the anterior and posterior leaflet is set to be 6.233 MPa and 2.087 MPa respectively.

The results of the automatic personalization at each level compared to a semi-manual patient-customization method are shown in Table 2.

TABLE 2

| (mm) | Chordae I | Chordae II | Chordae III | Chordae IV | Final | Semi-Mannual |
|---|---|---|---|---|---|---|
| Patient 1 | 1.49 ± 0.83 | 1.46 ± 0.84 | 1.46 ± 0.84 | 1.46 ± 0.84 | 1.45 ± 0.84 | 1.47 ± 0.89 |
| Patient 2 | 2.98 ± 1.86 | 2.89 ± 1.88 | 2.47 ± 1.46 | 2.47 ± 1.46 | 2.47 ± 1.46 | 2.25 ± 1.27 |
| Patient 3 | 1.87 ± 1.19 | 1.87 ± 1.18 | 1.86 ± 1.17 | 1.70 ± 1.07 | 1.66 ± 1.08 | 1.91 ± 1.18 |
| Patient 4 | 1.80 ± 1.20 | 1.79 ± 1.21 | 1.79 ± 1.21 | 1.69 ± 1.14 | 1.55 ± 1.09 | 1.74 ± 1.34 |
| Patient 5 | 2.09 ± 1.36 | 2.05 ± 1.35 | 2.04 ± 1.35 | 2.04 ± 1.35 | 2.04 ± 1.35 | 2.27 ± 1.40 |

The automatic algorithm performs similarly if not better than the semi-manual method with an expert adjusting the chordae rest length and the EKF adjusting the material parameters. The average fitting error is 1.84±1.17 mm. Most patients achieve a good match at the coarse level of chordae adjustment. Some patients do not require fine tuning for the chordae. The adjustment of the chordae rest length brings the leaflet to the matching surface from the morphological perspective and reduces the average distances to about 2 mm, which is comparable to the error of the image observation from the quantitative perspective. The first step adjustment provides a better starting point to estimate the patient-specific material parameters to reduce the distance even further.

FIG. 5 shows the distances between the personalized model and the image based estimation as the ground truth in the form of a color-map from both top and side views. It can be seen that the patient-specific model simulates the mitral valve closure very closely to image based estimation. The matching is especially close in the mitral annulus region thanks to the use of the boundary conditions. The performance of the algorithm may be improved in certain regions by employing the cost function with related terms.

The estimated patient-specific material parameters are shown in table 2.

TABLE 2

| | $E_{ALf}$ | $E_{ALf}\perp$ | $G_{AL}$ | $E_{PLf}$ | $E_{PLf}\perp$ | $G_{PL}$ |
|---|---|---|---|---|---|---|
| P1 | 6.28 | 2.37 | 2.11 | 2.21 | 1.99 | 0.74 |
| P2 | 6.23 | 2.35 | 2.09 | 2.09 | 1.89 | 0.70 |
| P3 | 5.73 | 2.16 | 1.93 | 4.58 | 4.14 | 1.54 |
| P4 | 3.60 | 1.36 | 1.21 | 2.34 | 2.11 | 0.78 |
| P5 | 6.23 | 2.35 | 2.09 | 2.09 | 1.89 | 0.70 |

The anterior leaflet shows stiffer properties compared to the posterior leaflet for all patients. The general material parameters are also the optimized estimation for two patients. Different initial values of Young's moduli are used here but reach the same estimate.

Figure 6:
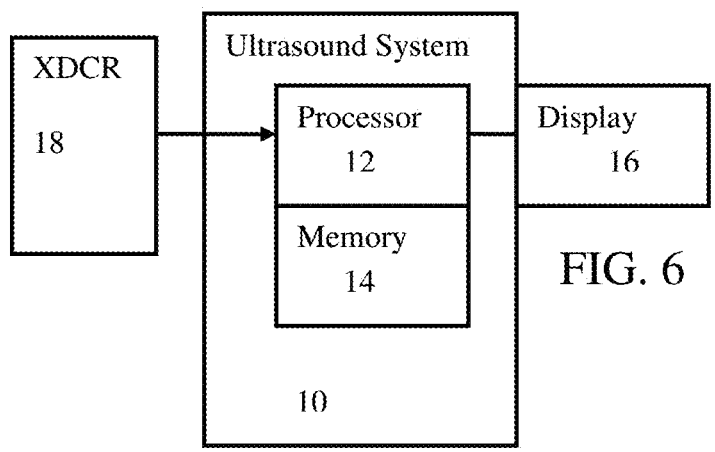
FIG. 6 is a block diagram of one embodiment of a system for estimating a mechanical property of anatomy.

FIG. 6 shows a system for estimating a mechanical property of anatomy. The system includes a transducer 18, an ultrasound scanner 10, and a display 16. The ultrasound scanner 10 includes a processor 12 and a memory 14. In alternative embodiments, the system is a CT scanner, MR scanner, or other imaging system. In yet other embodiments, the system is a workstation, computer, or server for simulating using data acquired by a separate system in real-time or using previously acquired patient-specific data stored in a memory. For example, an ultrasound scanner 10 is provided for acquiring ultrasound data representing a volume, and a separate database, server, workstation, and/or computer is provided for creating a model, detecting anatomy, and/or calculating patient-specific material properties. Additional, different, or fewer components may be used.

The ultrasound scanner 10 includes a transmit beamformer, receive beamformer, B-mode detector, Doppler detector, harmonic response detector, contrast agent detector, scan converter, filter, combinations thereof, or other now known or later developed medical diagnostic ultrasound system components. As another example, the transducer 18 is not provided, such as where the system is a workstation for off-line or later measurement of valve anatomy.

The transducer 18 is a piezoelectric or capacitive device operable to convert between acoustic and electrical energy.

The transducer 18 is an array of elements, such as a multi-dimensional or two-dimensional array. Alternatively, the transducer 18 is a wobbler for mechanical scanning in one dimension and electrical scanning in another dimension. In another embodiment, the array is a one-dimensional array on a cardiac catheter or a TEE probe. Multi-dimensional arrays or a plurality of one-dimensional arrays may be provided on a TEE probe.

The ultrasound scanner 10 uses the transducer 18 to scan a heart volume of a patient. Electrical and/or mechanical steering allows transmission and reception along different scan lines in the volume. Any scan pattern may be used. For example, a plurality of different planes through the heart is scanned by rotating a TEE array, moving a catheter array, or volume scanning with a matrix array. In one embodiment, the transmit beam is wide enough for reception along a plurality of scan lines. In another embodiment, a plane, collimated or diverging transmit waveform is provided for reception along a plurality, large number (e.g., 16-64 receive beams), or all scan lines.

The scan provides the medical diagnostic ultrasound data representing the heart, part of the heart, or valve volume (e.g., mitral valve) at different times as a sequence. The scan is repeated to provide data for the volume at different times. Ultrasound data representing a volume is provided in response to the scanning. The ultrasound data is beamformed, detected, and/or scan converted. The ultrasound data may be in any format, such as polar coordinate, Cartesian coordinate, a three-dimensional grid, two-dimensional planes in Cartesian coordinate with polar coordinate spacing between planes, or other format. The ultrasound data may be of any type, such as B-mode, flow mode (e.g., PW Doppler), spectral mode (e.g., CW Doppler), Doppler mode, contrast agent, harmonic, or other ultrasound modes of imaging.

The memory 14 is a buffer, cache, RAM, removable media, hard drive, magnetic, optical, database, or other now known or later developed memory. The memory 14 is a single device or group of two or more devices. The memory 14 is shown within the system 10, but may be outside or remote from other components of the system 10.

The memory 14 stores the ultrasound data, such as ultrasound data representing a heart or valve volume at different times in a heart cycle. The heart volume includes at least one valve, but other portions of the heart or other anatomy may be represented. The memory 14 stores flow (e.g., velocity, energy or both), spectral, and/or B-mode ultrasound data. Alternatively, the medical image data is transferred to the processor 12 from another device. The medical image ultrasound data is a three-dimensional data set, or a sequence of such sets. The data represents a three-dimensional region. Any format may be used, such as voxels interpolated to a three-dimensional grid or data representing parallel or non-parallel planes. For CW or PW Doppler, the ultrasound data may represent a volume, an area, a line, or a point.

For real-time imaging, the ultrasound data bypasses the memory 14, is temporarily stored in the memory 14, or is loaded from the memory 14. Real-time imaging may allow delay of a fraction of a second, or even seconds, between acquisition of data and imaging with measurements. For example, real-time imaging is provided by generating the images substantially simultaneously with the acquisition of the data by scanning. While scanning to acquire a next or subsequent set of data, images and measurements are generated for a previous set of data. The imaging occurs during the same imaging session or patient appointment used to acquire the data. The amount of delay between acquisition and imaging for real-time operation may vary, such as a greater delay for initially locating valve anatomies with less delay for measurements. In alternative embodiments, the ultrasound data is stored in the memory 14 from a previous imaging session and used for measuring.

The memory 14 is additionally or alternatively a non-transitory computer readable storage medium with processing instructions. The memory 14 stores data representing instructions executable by the programmed processor 12 for estimating a mechanical property of anatomy. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 12 is a general processor, digital signal processor, three-dimensional data processor, graphics processing unit, application specific integrated circuit, field programmable gate array, digital circuit, analog circuit, combinations thereof, or other now known or later developed device for estimating a mechanical property of anatomy. The processor 12 is a single device, a plurality of devices, or a network. For more than one device, parallel or sequential division of processing may be used. Different devices making up the processor 12 may perform different functions, such as an automated anatomy detector and a separate device for performing measurements associated with the detected anatomy. In one embodiment, the processor 12 is a control processor or other processor of a medical diagnostic imaging system, such as a medical diagnostic ultrasound imaging system processor. The processor 12 is configured by or operates pursuant to stored instructions to perform various acts described herein, such as detecting anatomy, defining a biomechanical model, inversely solving for patient-specific material properties, categorizing, and/or generating and displaying an image.

In one embodiment, the processor 12 is configured by software and/or hardware to perform inverse analysis. Valve dynamics are derived from the medical diagnostic ultrasound data. The dynamics or motion may be represented by position at different times or displacement between positions at different times. The processor 12 is configured to combine the valve dynamics with a biomechanical model. The position of the valve at one time is used to load the biomechanical model. The displacement is also used as part of the biomechanical model. One or more mechanical properties of tissue of the valve of the patient are variables in the biomechanical model. As part of the inverse solution, the processor 12 estimates the mechanical property from the combination of the observed dynamics with the created biomechanical model. A difference between the observed position or displacement and the valve kinematics calculated from the biomechanical model with any currently estimated mechanical property is interpolated. The determined difference is used by the processor 12 to refine motion estimation by the biomechanical model. The currently estimated mechanical property is altered as part of the estimation, and the results of the alteration on the motion output by the biomechanical model are again compared with and differences interpolated from the observed motion or dynamics. Any inverse solution may be used for iteratively determining the mechanical property, such as the processor 12 performing the inverse solution with a Kalman filter.

The processor 12 may generate an image. The biomechanical model is used to generate an image. The patient-specific scan data may be used for imaging. The image provides a visualization of the heart or valve that is a function of the determined patient-specific mechanical property.

The display 16 is a CRT, LCD, plasma, projector, printer, or other output device for showing an image. The display 16 displays an image of the detected anatomy, such as an image of a valve rendered from medical data and overlaid or highlighted based on the estimates of the valve position and/or mechanical property. The display 16 displays a sequence of renderings to generate a visualization of the valve motion through the sequence. The visualization may be generated during a same examination session as the scan. The detected anatomy may or may not be segmented, such as just displaying the valve.

Section II

Dense chordae representation is used to limit artifacts from representing the chordae with anatomical-based number of chordae. For example, the model discussed in Section I uses 28 chordae, which is a similar number to the number of chordae connected with a human mitral valve. In this section (Section II), the number of chordae is greater by at least a factor of two, such as using hundreds or thousands of chordae. While not anatomically accurate, the increased number of chordae in the model avoids dimple artifacts in the model and may better represent the effects of the branching and thickness variation in anatomically correct chordae.

Any of the geometric and/or biomechanical models of the mitral valve or other valve discussed in Section I may be used. Other models may be used. The geometrical model is personalized with data from non-invasive imaging modalities, such as Transesophageal Echocardiogram (TEE). The bio-mechanical model is built and used for interventional planning (e.g. modeling the effects of surgical repair or a minimally invasive cardiac procedure).

One embodiment of modeling using dense chordae is represented in FIG. 8. Dynamic three-dimensional images are acquired with non-invasive imaging modalities (e.g., TEE or computed tomography). The images are scan data representing the mitral valve. A geometric model of the mitral valve is extracted from a 3D image representing the valve at end diastole. Automatic or semi-automatic approaches may be used. The geometry is personalized based on the non-invasive 3D images.

A biomechanical model of the mitral valve is constructed from the geometric model. The bio-mechanical model parameterization contains various parameters (e.g., tissue stiffness, pressures, and/or others) and enables the computation of different physiological and dynamic behaviors. The biomechanical parameters of the mitral valve are personalized. Based on inverse-modeling techniques with the geometric model, unknown parameters such as tissue properties, pressures, and chordae rest lengths are optimized as part of personalization.

Using the biomechanical model as personalized, mitral valve interventional procedures are simulated using virtual computation. The effect of the procedure on valve closing at end systole may be simulated. Virtual mitral valve repair surgeries may be computed based on the model, such as edge-to-edge repair, annuloplasty, or other. The geometry of the valve resulting from intervention is provided by the biomechanical model for quantification and/or imaging. Thus, the model may be utilized to select the best therapy for a specific patient or for other purpose.

FIG. 7 shows one embodiment of a method for valve modeling from medical scan data. The method uses biomechanical and/or geometric modeling of a valve, such as the modeling discussed above or in Section I. Other modeling may be used, such as modeling without the displacement calculations of Section I. The modeling includes a dense representation of chordae and/or inverse solution for the lengths of some chordae and not others.

The acts are performed in the order shown or different order. Additional, different, or fewer acts may be performed. For example, acts from FIGS. 1-3 are performed. As another example, act 76 is not performed. The model with the personalized chordae lengths is used for any purpose, such as planning, study, and/or intervention result analysis.

The acts are performed by the system of FIG. 6 or a different system. For example, an image processor performs acts 70-74 without any user input of locations and/or values of parameters of the model. A display, printer, or interface performs act 76. As another example, one or more of the acts are performed manually or semi-automatically with the image processor and a user input device.

In act 70, an image processor models the valve of the patient with a biomechanical model. In one embodiment, the biomechanical model is a finite element model, but other approaches may be used. The dynamic system having mass, damping, stiffness, displacement, velocity, and acceleration terms discussed in Section I may be used.

The model is personalized to a specific patient from medical image data representing the valve at a given time, such as end diastole. Data representing the valve over time may be used. In one embodiment for extracting mitral valve geometry from non-invasive modalities, an anatomical point distribution model of the mitral and its subvalvular apparatus is extracted from 3D echo or TEE data. This point distribution is the geometric model for that phase of the heart cycle.

Figure 9:
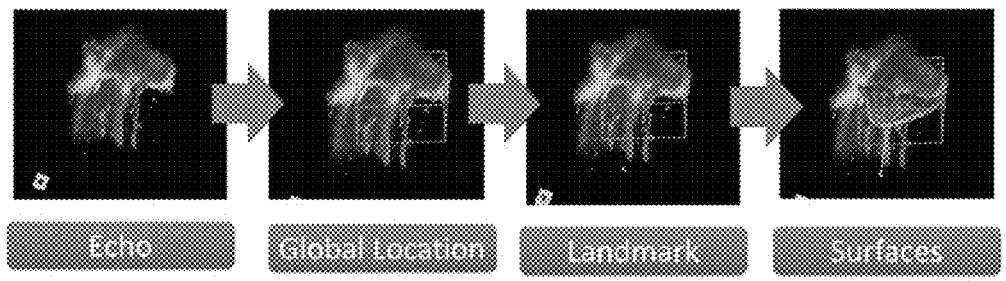
FIG. 9 illustrates a multi-level approach to personalizing a model to patient echo data.

As represented in FIG. 9, the geometric model is hierarchically parameterized with three hierarchy layers. On the coarsest layer, the global location of the mitral valve is represented as a bounding box. The second layer models the anatomy of the mitral valve with anatomical landmarks. Any landmarks may be used, such as two trigones, two commissures, one posterior annulus mid-point, two leaflet tips, and two papillary tips. The landmarks represent key or identifiable anatomical locations and are capable of capturing a broad spectrum of morphological and physiological variations of the mitral valve physiology. On the finest scale, the model is the MV annulus and the anterior and posterior leaflets represented as dense surface models. One surface model is a triangular mesh, but other surface representations may be used.

The geometric model is personalized using automatic or semi-automatic processing. For automatic, a machine-learnt segmentation may be used to automatically extract the parameters of the geometric model. For a semi-automatic approach, user or manual entry is used to initialize the geometric model in the in-vitro echo or ultrasound images. For example, a user first manually initializes the bounding box of the mitral valve and then positions the mitral valve landmarks. The image processor initializes and solves for the full surface model based on the landmarks. The final geometric mitral valve model may be further manually edited to match the images. The dense surface models of the mitral valve, including anatomical landmarks, may be adjusted by the user.

Based on the geometry of the patient's valve, the image processor creates the biomechanical model. To simulate operation of the valve, such as closure, the anatomy (e.g., geometric model) determined from the echo data is used. The dynamics system, represented as:

$$M\ddot{U}+C\dot{U}+K\ddot{U}=f_t+f_p+f_c$$

is solved, where M is the diagonal mass matrix calculated from the mass density $\rho=1040$ g/L, C is the Rayleigh damping matrix with coefficients 1e4 s$^{-1}$, and 0.1 s for the mass and stiffness matrix respectively, K is the stiffness matrix, $f_t$ is the force created by the chords on the leaflets, $f_p$ the pressure force, $f_c$ the contact forces, and U is the displacement vector of the mitral valve vertices of the surface mesh, $\dot{U}$ is the velocity vector, and $\ddot{U}$ is the acceleration vector. Other dynamic systems may be used. Transverse isotropic linear tissue elasticity, implemented using a co-rotational finite elements method, is relied on to cope with large deformations.

Some of the parameters of the biomechanical model use averaged or constant values. In one embodiment, the Poisson ratio is set as θ32 0.488 for both leaflets, fiber Young's modulus is $E_{AL}=6.23$ MPa and $E_{PL}=2.09$ MPa for the anterior and posterior leaflets, cross-fiber Young's modulus is $E_{AL}=2.35$ MPa and $E_{PL}=1.88$ MPa, and shear modulus is 1.37 MPa. Other values may be used. Alternatively, one or more of the tissue characteristics are personalized, such as inversely solving for Young's modulus in addition to chordae length.

Figure 10:
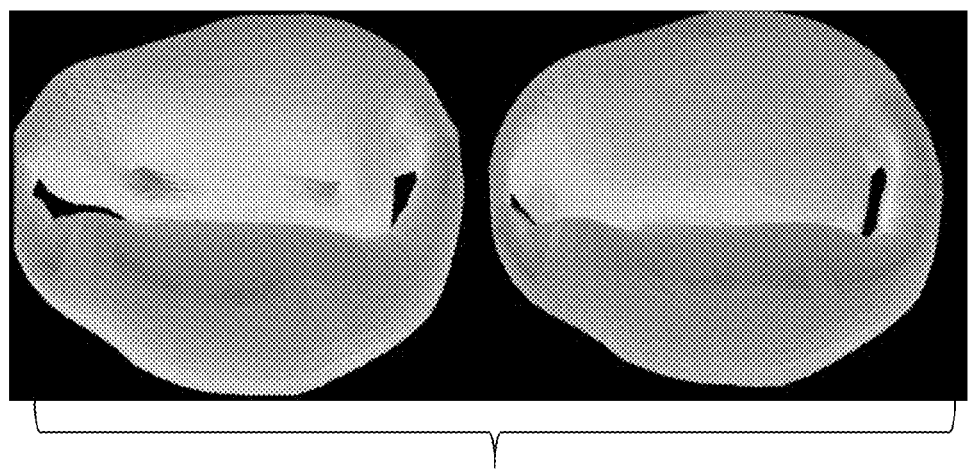
FIG. 10 shows an artifact from modeling with chordae emulating human anatomy and lack of the artifact from modeling with dense chordae.

Modeling with a few chordae, such as 28 chordae in a sparse representation, may result in artifacts. In the example in Section I, the chordae are evenly attached at the free-edges of the leaflets and four chordae are tethered at the base of the leaflets. For a given leaflet, two chordae are modeled as connecting with a leaflet away from the edge. As a result, the chordae tend to create dimples in the leaflet. FIG. 10, left side, shows modeling of closure of the mitral valve using a 10 chordae example, resulting in two dimples in the leaflet. To avoid the artifact and compute closure more accurately, the chordae are modeled as a dense representation. The number of chordae is denser, such as modeling more chordae than found in human anatomy. The number of chordae is greater than a factor of two or more, such as at least 1,000 chordae. For example, more chordae by factor of ten or more are included in the finite element model than in the anatomy of the patient.

The dense representation attaches chordae throughout the leaflet. For example, chordae attach to the edges, but also to ten or more locations away from the edges even though actual chordae may not connect at those location. In one embodiment, a chorda is modeled as attaching to each vertex in the mesh representation of the leaflet surface. For example, each node of a triangular mesh connects with a chorda. Other spatial distributions of connections of separate chordae to leaflet locations may be used. In one embodiment, 87 marginal and 1500 basal chordae per leaflet connect to the related papillary tip. Other numbers may be used.

FIG. 10, right side, shows modeling of mitral valve closure with the dense chordae. The dimple artifact is not present or is less visible. The bulging of the anterior and posterior leaflet is more natural using the dense model compared to the sparse model.

Since a dense representation is used, the chordae may be grouped for processing. Any number of groups may be used. For example, four or more groups are defined. Each group represents a different spatial region of the leaflet. Grouping based on papillary tip or other location may be used instead or additionally. In one embodiment, the groups are the anterior basal, anterior marginal, posterior basal, and posterior marginal locations. Other groupings may be used. At least 100 chordae are provided in each group, but other numbers may be used.

Figure 11:
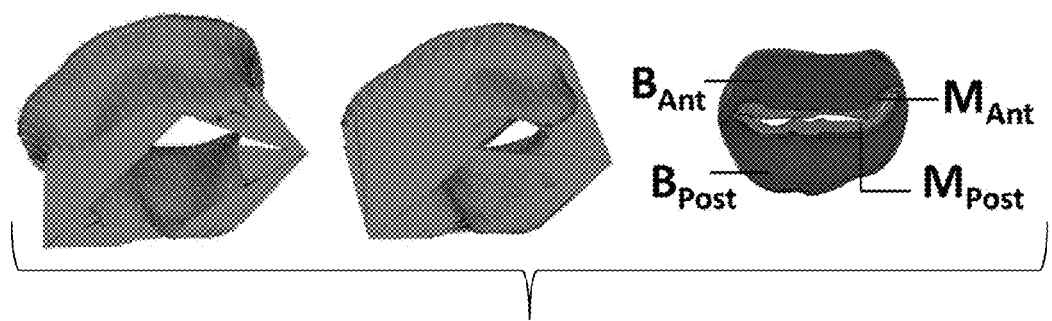
FIG. 11 illustrates dense chordae and regions used for inverse solution.

FIG. 11 shows an example visualization of the dense chordae model. The left image shows the marginal regions of the dense chordae model and the middle image the basal chordae regions. Due to the density of over a thousand chordae, the chordae appear as a wall. Ridges are added for visualizing the direction of the chordae. The right image shows the subdivision of the four regions among the anterior and posterior leaflet ($B_{Ant}$, $M_{Ant}$, $B_{Post}$, $M_{Post}$).

To determine the chordae length, such as the rest length, for a particular patient, the image processor performs an inverse solution in act 72. Any optimization may be used for the inverse solution, such as a gradient-free optimization. In one embodiment, a bound optimization by quadratic approximation is used.

The grouping of the chordae is used in the solution. Rather than solve for the length of all the chordae, the length of a fewer number of chordae are solved. For example, length of one or more but less than all the chordae in each group is determined by inverse solution. The sub-set for inverse solution is fewer than all of the chordae by a factor of two or more (e.g., by a factor of 10 or more). In one embodiment, a single chorda length is found for each group using the inverse solution. The single chorda is any one of the many chordae of the group or is a generalized singular representation of a chorda for the region. In another embodiment, the lengths of the 28 chordae discussed in Section I are determined by inverse solution. By solving length for just a sub-set of the chordae, the amount of processing and corresponding time to personalize the model is reduced. By solving for the length of just one chorda per group, the amount of processing and time is greatly reduced.

The chordae for which length is found through inverse solution are particular ones of the dense representation. Alternatively, the model is simplified to include only the sub-set or lesser number of chordae. The inverse solution solves for all of the chordae in this simplified model, but not all of the chordae to be used in the full model. In yet another alternative, the chordae for which length is found through inverse solution are representative ones not necessarily with an exact match to any of the ones of the dense representation.

In the four-region example above, the lengths of one or only some of the chordae in each anterior basal, anterior marginal, posterior basal, and posterior marginal region are determined through inverse solution. The inverse solution is applied for the four leaflet regions, but not for all of the chordae in each region. During the iterative optimization, the optimal values for chordae rest lengths for each region—$B_{Ant}$, $M_{Ant}$, $B_{Post}$, $M_{Post}$ of the bio-mechanical model are determined iteratively. The model of Section I is extended to allow personalization of the chordae rest length for each chordae region.

For inverse solution, the image processor uses differences between the geometric model at one time with the simulation of the biomechanical model for that time. For example, geometric models are based on locations of anatomy at end diastole and end systole. The end diastole geometric model with or without information from other times is used to create the biomechanical model. The biomechanical model is then used to simulate closure at end systole. The ultrasound-based geometric model at end systole (e.g., the anatomy locations determined from echo data at end systole) is compared with the biomechanical model simulation at end systole. The differences are used in a cost function to guide optimization of the biomechanical model (e.g., chordae lengths) to more accurately represent the particular patient.

The differences are based on locations of the surface, such as locations of the mesh nodes. The differences are alternatively or additionally based on other features of the valve geometry.

The differences are used in a cost function for optimization. Any differences may be used. For example, one or more of an average distance between meshes, a maximum distance between meshes, a length of leaflet contact at closure, coaptation area of leaflets at closure, average height of coaptation (e.g., a distance across closure area), anterior leaflet length, and/or posterior leaflet length are used. The difference between the same measure for the biomechanical model and the geometric model is included in the cost function. In one embodiment, two, three, or more (e.g., all) of the difference measures are used in the cost function. Any combination, such as a weighted average or sum, may be used.

The cost function is determined by the difference between the annotated mitral valve model (i.e., geometric model) in the systolic (closed) state and the simulated mitral valve model at closure based on the bio-mechanical model. Comparison may be at other phases in addition or instead of the closed state. In one embodiment, the cost function used to determine the adjustment or update of the chordae lengths in the next iteration is represented as:

$$CF = \alpha^* distAvg + \beta^* distHausdorff + \gamma^* distClosureLength + \delta^* distCoaptAvgHeight + \epsilon^* distCoaptArea + \rho^* distLeaf AvgLengthAnt + \sigma^* distLeaf AvgLengthPost$$

where distance is a difference between the biomechanical and geometric models at closure (e.g., end systole), distAvg is the average point-to-mesh distance, distHausdorff is the Hausdorff metric measuring the maximum mesh distance, distClosureLength is the MV closure line length distance, distCoaptArea is the mitral valve coaptation area distance, and distLeaf AvgLengthAnt,distLeafAvgLengthPost are the mitral valve anterior and posterior leaflet length distances.

This cost function is a linear combination of both geometric and clinical measurements to quantify the goodness of fit of the computed closure model with the geometric model for the time of closure. The weights are empirically determined values, such as $\alpha=0.2$, $\beta=0.2$, $\gamma=0.1$, $\delta=0.2$, $\epsilon=0.07$, $\rho=0.2$ and $\sigma=0.2$. Other weight values may be used. Other cost functions may be used.

Using the cost function, the optimization determines changes to the chordae lengths in the inverse solution. Once the cost function reaches a minimum or is below a threshold, the lengths of the chordae are selected as the personalized values for the biomechanical model. The lengths of the subset of chordae have been inversely determined.

In act 74, the image processor derives values for the other chordae lengths. Inversion solution is used for a sub-set, but the modeling uses the dense representation. The lengths for the sub-set of chordae are used to determine the lengths for the other chordae.

The location of the other chordae relative to the chordae for which lengths have been solved is used. Using a function, the lengths chordae for given locations are related to the solved length. In the regional example, a function relates the lengths of the chordae throughout the region to the length of the chordae solved for that region. The spatial relationship of the chordae is used to map the lengths. For example, the length of a chorda solved for one region is mapped to lengths distributed about the region of the leaflet. Where the solved chorda length is for a particular location of connection with the leaflet, the relative location to that location is used to determine length. Where the solved chorda length is for the region in general, the position of the chordae for which length is being determined is mapped from the regional length. Alternatively, the location of the chordae is used, but without specific relation to the location of the inversely solved chordae.

Any function may be used, such as a non-linear or linear function stored as a look-up table. The function may be based on empirical information, such as rendering or modeling results having tested different functions. The function may alternatively or additionally be based on geometric or anatomic information, such as the curvature or expected distance of the location on the leaflet from the papillary tip in a particular state (e.g., resting state). The function captures the relative differences in resting state length for different chordae within the region.

As an alternative to a look-up table, a mathematical function relates the lengths of the chordae for each region to the solved chorda or chordae length for that region. For example, the function provides weights for the locations. The solved for length is weighted for each location to derive the length for that location. The value for the solved for length is adjusted by multiplication by the weight, but division, subtraction, and/or addition may be used.

In one embodiment, the image processor adjusts the values for the sub-set (i.e., inversely solved for values) based on a distance between a papillary tip and a vertex for the chordae at a given cardiac phase, a shortest distance in a region between the papillary tip and vertices of the region, and a longest distance in the region between the papillary tip and the vertices of the region. The vertices are the nodes of the mesh to which the chordae of the region connect. In the four region example (e.g., $B_{ani}$—anterior leaflet basal chordae, $M_{ani}$—anterior leaflet marginal chordae, $B_{pos}$—posterior leaflet basal chordae, $M_{pos}$—posterior leaflet marginal chordae), a mathematical function is used to avoid having the same rest length for all tensile springs (i.e., dense chordae of the model) within one region. For example, the specific rest length of each chordae in the region is adjusted based on the following formula:

$$rl_x = \left(1 + \frac{x-s}{l-s}\right) rl_{optimized}$$

where $rl_x$ is the rest length of an individual tensile spring (i.e., other chorda), x represents the distance between the papillary tip to vertex on the leaflet for the chorda, s the shortest distance between the papillary tip and any vertex in the leaflet region, l the longest distance between the papillary tip and any vertex in the leaflet region, and $rl_{optimized}$ is the inversely solved rest length for the given region. Using the optimization to inversely solve for the region rest length, the rest lengths of the other chordae at the corresponding vertices are derived using the function. Other functions with the same or different terms may be used.

The derivation occurs after optimization. The iterations are performed to find a best match without the dense chordae. Alternatively, the derivation is performed at each iteration of the optimization. The cost function differences between the biomechanical model with the previously solved and derived dense chordae lengths and the geometric model from the patient scan data includes the influence of the dense chordae.

Other considerations may be included in the iterations of the optimizations or after optimization of one or more parameters (e.g., chordae rest length). For example, self-collusion is modeled. The leaflets contact each other. To regulate the contact, the collusion is modeled with a collusion stiffness (e.g., 100 kPa) and friction coefficient (e.g., 0.1).

In act 76, the operation of the valve is indicated. The biomechanical model, using the values of the chordae lengths as solved for in optimization and as derived from solved lengths, is used to show valve operation.

The operation is indicated through a calculated value, such as coaptation area. The biomechanical model simulates closure or position at another cardiac phase. Any characteristic may be quantified from the biomechanical model. For example, the chordae lengths are displayed.

Alternatively or additionally, the operation is indicated through an image. A two-dimensional cross-section image and/or a three-dimensional rendering of the valve are formed from the biomechanical model. The image may include the biomechanical model as an overlay of an image from the scan data or may be of the biomechanical model by itself. A sequence of images may be shown, where the biomechanical model at each phase of the sequence is used for the corresponding image.

The biomechanical model models using the dense chordae and corresponding values of lengths. The resulting quantity and/or image are responsive to the dense distribution of chordae and the various lengths of the chordae. For example, the right side of FIG. 10 shows a three-dimensional rendering from the biomechanical model where the leaflet surface and resulting contact area are based, in part, on the chordae lengths of the dense chordae. The valve at closure is represented by the biomechanical model, providing physicians with diagnostically useful information.

The indication may be used for planning. By observing the simulated position and/or operation of the valve, a physician may more easily determine undesired operation of the valve. The indication may be used for modeling treatment. The treatment is simulated by adding the treatment or effects of the treatment into the biomechanical model. For example, two locations on opposite leaflets are held in position, simulating a clip. The operation and/or position of the valve with the simulated clip are determined through simulation with the biomechanical model. The results of different clip placements may be observed for planning treatment.

Referring again to FIG. 6, the system of FIG. 6 may be used for valve modeling with dense chordae and inverse solution of fewer than all the chordae in the biomechanical model. The ultrasound scanner 10 is configured to scan the heart volume of a patient, such as a TEE scan, using the transducer 18. The scan provides medical diagnostic ultrasound data representing at least part of the heart, such as the mitral valve.

The memory 14 includes instructions for valve modeling by the image processor 12. The image processor 12 is configured to inversely solve for a chordae length or lengths in each of multiple zones and determine other chordae lengths in each of the multiple zones from the solved lengths for the respective zone. The chordae lengths are solved in two stages or differently. Some lengths use the optimization with inverse solution. The other lengths are derived from the solved lengths, whether used in cost function calculation or not. The number of chordae used in the model and for which lengths are determined is greater than a number found in a human valve, such as by a factor of two or more.

The display 16 is configured to generate a visualization based on the chordae lengths and any other parameters of the biomechanical model. The visualization is an image of the model, sequence of images of the model over time, and/or quantity.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for valve modeling from medical scan data, the method comprising:
    modeling, by a processor, a valve of a patient with a biomechanical model, which is a function of chordae lengths for a dense number of chordae relative to human anatomy comprising at least 1,000 chordae, from first medical image data representing the valve at a first time;
    inversely solving, by the processor, for values of a sub-set of the chordae lengths of the valve as a function of differences between locations of the biomechanical model simulated for a second time and second anatomy locations detected from second medical image data representing the valve at the second time;
    deriving values of the chordae lengths for chordae lengths other than the sub-set from the values of the chordae lengths for the subset; and
    indicating valve operation from the biomechanical model with the values of the chordae lengths for the sub-set and the others.

2. The method of claim 1 wherein modeling comprises modeling with the biomechanical model comprising a finite element model.

3. The method of claim 1 wherein modeling comprises modeling with the biomechanical model comprising a dynamic system having mass, damping, stiffness, displacement, velocity, and acceleration terms.

4. The method of claim 1 wherein modeling comprises modeling with a surface mesh for leaflets, chordae modeled as connecting with each node of the surface mesh.

5. The method of claim 1 wherein solving comprises solving with gradient-free optimization.

6. The method of claim 1 wherein solving comprises solving as a function of a cost function representing the differences as one or more of differences in an average distance, a maximum distance, a length of leaflet contact, coaptation area, average height of coaptation, anterior leaflet length, and posterior leaflet length.

7. The method of claim 6 wherein solving comprises solving with the cost function including three or more of the differences.

8. The method of claim 1 wherein solving comprises solving with the sub-set comprising anterior basal, anterior marginal, posterior basal, and posterior marginal.

9. The method of claim 1 wherein solving comprises solving with the sub-set comprising fewer than all of the number of chordae by a factor of 10 or more.

10. The method of claim 1 wherein deriving the values comprises adjusting the values for the sub-set based on a distance between a papillary tip and a vertex for the chordae at the first time, a shortest distance in a region between the papillary tip and vertices of the region, and a longest distance in the region between the papillary tip and the vertices of the region.

11. The method of claim 1 wherein deriving the values comprises, for each chordae, weighting one of the values of the subset.

12. The method of claim 1 wherein indicating comprises displaying an image of the valve, the image being a function of the values of the chordae lengths.

13. The method of claim 1 wherein indicating comprises displaying valve closure with the biomechanical model using the values of the chordae lengths.

14. A non-transitory computer readable storage medium having stored therein data representing instructions executable by a programmed processor for valve modeling, the storage medium comprising instructions for:
modeling a valve of a patient with a finite-element model, the finite-element model including at least 100 chordae in each of at least four regions of the valve with the finite-element model including nodes of a mesh for each leaflet, one of the chordae being assigned to each node of the mesh for each of the leaflets;
inversely solving for lengths of one of the chordae in each of the at least four regions; and
calculating lengths of others of the chordae in each of the at least four regions based on the regions of which the chordae are members and the corresponding lengths for the one of the chordae.

15. The non-transitory computer readable storage medium of claim 14 wherein inversely solving comprises inversely solving for four leaflet regions.

16. The non-transitory computer readable storage medium of claim 14 wherein calculating comprises mapping the lengths of the others from a spatial relationship to the length of the one for the corresponding region.

17. A system for valve modeling from medical scan data, the system comprising:
an ultrasound scanner configured to scan a heart volume of a patient, the scan providing medical diagnostic ultrasound data representing at least a part of the heart;
a processor configured to generate a model from the medical diagnostic ultrasound data with a surface mesh for leaflets, the model including chordae as connecting with each node of the surface mesh, the processor configured to solve using the model for a first chordae length in each of multiple zones and determine other chordae lengths in each of the multiple zones from the first chordae length for the respective zone;
a display configured to generate a visualization based on the first and the other chordae lengths.

18. The system of claim 17 wherein the first chordae and other chordae are a number of chordae greater than anatomical chordae of the patient by a factor of at least two.

19. A method for valve modeling from medical scan data, the method comprising:
modeling, by a processor, a valve of a patient with a biomechanical model, which is a function of chordae lengths for a dense number of chordae relative to human anatomy from first medical image data representing the valve at a first time;
inversely solving, by the processor, for values of a sub-set of the chordae lengths of the valve as a function of differences between locations of the biomechanical model simulated for a second time and second anatomy locations detected from second medical image data representing the valve at the second time;
adjusting the values for the sub-set based on a distance between a papillary tip and a vertex for the chordae at the first time, a shortest distance in a region between the papillary tip and vertices of the region, and a longest distance in the region between the papillary tip and the vertices of the region;
deriving values of the chordae lengths for chordae lengths other than the sub-set from the adjusted values of the chordae lengths for the subset; and
indicating valve operation from the biomechanical model with the values of the chordae lengths for the sub-set and the others.

* * * * *